(12) United States Patent
Swanson

(10) Patent No.: US 10,286,031 B2
(45) Date of Patent: May 14, 2019

(54) METHOD OF MANUFACTURE OF GNRH-CONTAINING GEL

(71) Applicant: UNITED-AH II, LLC, Sheridan, IN (US)

(72) Inventor: Mark E. Swanson, Princeton Junction, NJ (US)

(73) Assignee: UNITED-AH II, LLC, Sheridan, IN (US)

( * ) Notice: Subject to any disclaimer, the term of this patent is extended or adjusted under 35 U.S.C. 154(b) by 0 days.

(21) Appl. No.: 15/303,438

(22) PCT Filed: Apr. 17, 2015

(86) PCT No.: PCT/US2015/026487
§ 371 (c)(1),
(2) Date: Oct. 11, 2016

(87) PCT Pub. No.: WO2015/161263
PCT Pub. Date: Oct. 22, 2015

(65) Prior Publication Data
US 2017/0035834 A1   Feb. 9, 2017

Related U.S. Application Data

(60) Provisional application No. 62/026,153, filed on Jul. 18, 2014, provisional application No. 61/981,370, filed on Apr. 18, 2014.

(51) Int. Cl.
| | | |
|---|---|---|
| *A61K 38/09* | (2006.01) |
| *A61K 38/25* | (2006.01) |
| *A61K 47/02* | (2006.01) |
| *A61K 47/12* | (2006.01) |
| *A61K 47/18* | (2017.01) |
| *A61K 9/06* | (2006.01) |
| *A61K 47/38* | (2006.01) |
| *A61K 47/20* | (2006.01) |

(52) U.S. Cl.
CPC ............. *A61K 38/09* (2013.01); *A61K 9/06* (2013.01); *A61K 38/25* (2013.01); *A61K 47/02* (2013.01); *A61K 47/12* (2013.01); *A61K 47/183* (2013.01); *A61K 47/20* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 6,503,534 B1 * | 1/2003 | Pellet | A61K 9/0024 424/422 |
| 8,905,913 B2 * | 12/2014 | Webel | A61K 38/09 600/33 |
| 2012/0046519 A1 * | 2/2012 | Webel | A61K 38/09 600/35 |

OTHER PUBLICATIONS

Sarkar (Journal of Applied Polymer Science, vol. 24, 1073-1087) (Year: 1979).*
Lancaster (downloaded from URL:< https://www.lancasterprd.com/high-shear-mixer-additional-info/>, Aug. 24, 2010 (Year: 2010).*

\* cited by examiner

*Primary Examiner* — Sergio Coffa
(74) *Attorney, Agent, or Firm* — Barnes & Thornburg LLP

(57) ABSTRACT

The invention relates to compositions for synchronizing the time of insemination in an animal. More particularly, the invention relates to a process for manufacturing and stabilizing GnRH-containing compositions for use in synchronizing the time of insemination in an animal.

17 Claims, 10 Drawing Sheets

BULK UNIFORMITY SAMPLING LOCATIONS

EXAMPLE SAMPLING LOCATIONS

METHOD OF MANUFACTURE OF GNRH-CONTAINING GEL

CROSS REFERENCE TO RELATED U.S. PATENT APPLICATIONS

This application is a national stage entry under 35 U.S.C. § 371(b) of PCT International Application No. PCT/US2015/026487, filed Apr. 17, 2015, and claims priority under 35 U.S.C. § 119(e) to U.S. Provisional Application Ser. No. 61/981,370, filed Apr. 18, 2014 and U.S. Provisional Application Ser. No. 62/026,153, filed Jul. 18, 2014, the disclosures of which are incorporated herein by reference.

FIELD OF THE INVENTION

The invention relates to compositions for synchronizing the time of insemination in an animal. More particularly, the invention relates to a process for manufacturing and stabilizing such compositions.

BACKGROUND OF THE INVENTION

Gonadotropin-releasing hormone (GnRH) is a peptide of 10 amino acids and is also known as luteinizing-hormone releasing hormone (LHRH). Gonadotropin-releasing hormone is produced in the hypothalamus, and is responsible for the release of follicle-stimulating hormone and luteinizing hormone from the pituitary gland. Gonadotropin-releasing hormone is released from neurons in the hypothalamus, and plays a role in the complex regulation of follicle-stimulating hormone and luteinizing hormone release. Follicle-stimulating hormone and luteinizing hormone, in combination, regulate the functioning of the gonads to produce testosterone in the testes and progesterone and estrogen in the ovaries, and regulate the production and maturation of gametes. For example, follicle-stimulating hormone stimulates the growth and recruitment of immature ovarian follicles in the ovary, and luteinizing hormone triggers ovulation.

Gonadotropin-releasing hormone has been isolated and characterized as a decapeptide. Synthetic forms of gonadotropin-releasing hormone are available and modifications of the decapeptide structure of gonadotropin-releasing hormone have led to multiple gonadotropin-releasing hormone analogs that either stimulate (e.g., gonadotropin-releasing hormone agonists) or suppress (e.g., gonadotropin-releasing hormone antagonists) the release of the gonadotropins, such as luteinizing hormone and follicle-stimulating hormone.

It is important to commercial swine production to maximize reproductive efficiency to make swine production more profitable. There has been heavy reliance on daily heat detection of individual female swine with the associated labor costs devoted to manual detection of heat in the female swine based on daily checks of gilts or sows to achieve the best results with, for example, artificial insemination. Heat detection using labor intensive methods, such as daily checks, increases the probability of success with artificial insemination. Thus, devoting time, manual labor, and materials costs to daily checks for heat detection is necessary because it is difficult to predict the time of heat and ovulation (i.e., in order to determine the best time for insemination) without using methods requiring a daily regimen for monitoring heat detection. Accordingly, compositions are needed to optimize the success of insemination of animals, to reduce or eliminate the need for heat detection, to reduce the labor costs, and to increase the profitability of swine production.

Applicants have discovered a gonadotropin-releasing hormone composition in a gel useful for controlling the time of ovulation via hormone administration, and that can eliminate breeding based on estrus detection and allow a swine to receive only one or two inseminations for optimal fertility and optimal cost expenditure. Improved manufacturing processes are needed to prepare larger, uniform commercial batch sizes of this GnRH-containing composition for synchronizing the time of insemination in an animal. Applicants have discovered methods of preparing such a GnRH-containing gel composition that result in increased uniformity of the composition.

SUMMARY OF THE INVENTION

Applicants have discovered an effective process for manufacturing a gel composition containing a gonadotropin-releasing hormone (GnRH) or a GnRH agonist, denoted as a gonadotropin releasing hormone containing gel, a GnRH-containing gel, a GnRH-containing drug product, or a GnRH-containing gel composition. More specifically, Applicants have discovered an improved manufacturing process for production of uniform larger batch sizes of the GnRH-containing gel composition. The improved process facilitates preparation of a uniform, larger batch size of the GnRH-containing gel.

In the preparation of the GnRH-containing gel, the gonadotropin releasing hormone and other, optional, components, such as a preservative, a stabilizer, a tonicity agent, and a buffering agent, are typically mixed in water to provide an aqueous mixture. To this mixture, with continued stirring, is added a gelling agent, such as methyl cellulose, and the resulting mixture is stirred under high shear mixing conditions (for example, at 450-570 RPM) to provide a mixture which is denoted in this application as a "primary compounding mixture batch," including that which is provided below in step a). This batch may then be transferred to a holding vessel prior to packaging. Uniformity of the batch is assured by sampling from various sites in the holding vessel, for example at the top center, at the top edge (at 0°, 90°, 180° and 270°), at the middle center, at the middle edge (at 0°, 90°, 180° and 270°), and at the bottom, see FIG. 1. It has been found that the high shear mixing step described above may be insufficient to assure uniformity of the product in the holding vessel when the procedure is carried out on a commercial scale, for example at the scale of 500 kg of gonadotropin releasing hormone.

In one embodiment of the invention, there is described a process for the manufacture of a gonadotropin releasing hormone containing gel from a primary compounding mixture batch of a drug product comprising the step of further mixing the (above described) primary compounding mixture batch with low shear mixing, for example using a counter motion mixer, using counter motion mixing (CMM) for the Final Compounding Phase.

In another embodiment of the invention, there is described a process for the manufacture of a gonadotropin releasing hormone containing gel comprising the above step of further mixing using CMM and a further step using CMM with cooling to 15° C. or below.

For the above embodiments comprising a step using CMM, a further embodiment comprises the step of holding the mixture at least about 24 hours at 2-8° C.

In one embodiment, a process for the manufacture of a gonadotropin releasing hormone containing gel is described.

The process comprises the steps of: a) providing a primary compounding mixture batch of a drug product comprising the gonadotropin releasing hormone in an aqueous mixture, further comprising: optionally, a preservative; optionally, a stabilizer; optionally, a tonicity agent; optionally, a buffering agent; and a gelling agent; b) further mixing the mixture using counter motion mixing (CMM); c) optionally, adjusting the pH of the mixture; d) further mixing the mixture using counter motion mixing (CMM) with cooling to 15° C. or below; e) optionally, filtering the mixture, and; f) holding the mixture at least 24 hours at 2-8° C.

In the above described embodiment, the following features, or any combination thereof, apply. In the above described embodiment: 1) the gonadotropin releasing hormone can have the formula

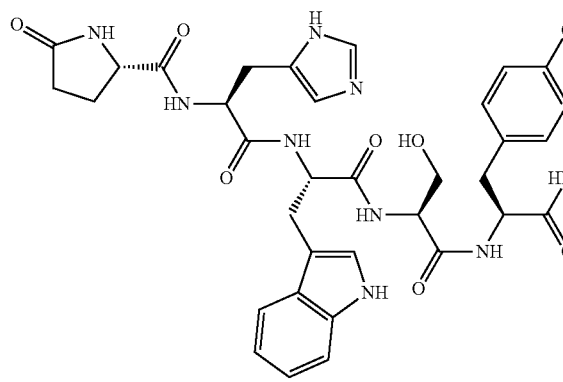
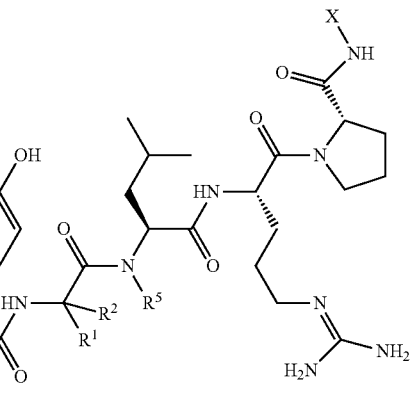

or a solvate, a hydrate, or a pharmaceutically acceptable salt thereof, wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle; $R^5$ is hydrogen or alkyl; and X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl; 2) the gonadotropin-releasing hormone can be selected from the group consisting of compounds of the formula above wherein a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R; b) $R^1$ is hydrogen, $R^2$ is hydrogen, X is $CH_2(CO)NH_2$; and $R^5$ is hydrogen; c) $R^1$ is 1H-1-benzyl-imidazol-4-yl-methyl, $R^2$ is hydrogen, X is ethyl; and $R^5$ is hydrogen; d) $R^1$ is 2-methylpropyl, $R^2$ is hydrogen, X is ethyl; and $R^5$ is hydrogen; e) $R^1$ is 2-naphthylmethyl, $R^2$ is hydrogen, X is $CH_2(CO)NH_2$; and $R^5$ is hydrogen; f) $R^1$ is t-butoxymethyl, $R^2$ is hydrogen, X is ethyl; $R^5$ is hydrogen; and the configuration of the carbon to which $R^1$ is attached is R; g) $R^1$ is benzyl, $R^2$ is hydrogen, X is $CH_2(CO)NH_2$; $R^5$ is hydrogen; and the configuration of the carbon to which $R^1$ is attached is R; h) $R^1$ is t-butoxymethyl, $R^2$ is hydrogen, X is $HN(CO)NH_2$; and $R^5$ is hydrogen; i) $R^1$ is 1H-indol-3-yl-methyl, $R^2$ is hydrogen, X is ethyl; and $R^5$ is hydrogen; j) $R^1$ is methyl, $R^2$ is hydrogen, X is hydrogen; $R^5$ is hydrogen; and the configuration of the carbon to which $R^1$ is attached is R; k) $R^1$ is 1H-indol-3-yl-methyl, $R^2$ is hydrogen, X is ethyl; $R^5$ is methyl; and the configuration of the carbon to which $R^1$ is attached is R; l) $R^1$ is methyl, $R^2$ is hydrogen, X is $CH_2(CO)NH_2$; $R^5$ is hydrogen; and the configuration of the carbon to which $R^1$ is attached is R; m) $R^1$ is 4-aminobutyl, $R^2$ is hydrogen, X is $HN(CO)NH_2$; $R^5$ is hydrogen; and the configuration of the carbon to which $R^1$ is attached is R; n) $R^1$ is methyl, $R^2$ is methyl, X is $HN(CO)NH_2$; and $R^5$ is hydrogen; and o) $R^1$ is ethyl, $R^2$ is hydrogen, X is hydrogen; $R^5$ is hydrogen; and the configuration of the carbon to which $R^1$ is attached is R; 3) the gonadotropin-releasing hormone can be triptorelin; 4) the hormone can be in acetate form; 5) the mixture can comprise a preservative wherein the preservative is selected from the group consisting of methylparaben and propylparaben; 6) the mixture can comprise a stabilizer wherein the stabilizer is L-methionine; 7) the mixture can comprise a tonicity agent wherein the tonicity agent is sodium chloride; 8) the mixture can comprise a buffering agent wherein the buffering agent is sodium citrate-citric acid; 9) the gelling agent can be a polysaccharide selected from the group consisting of celluloses, dextrans, and alginates; 10) the gelling agent can be a cellulose; 11) the cellulose can be methylcellulose; 12) the mixture can comprise about 0.5 weight % to about 4.0 weight % of methylcellulose; 13) the mixture can comprise about 1.2 weight % of methylcellulose; 14) the mixture can comprise triptorelin, methylparaben, propylparaben, L-methionine, sodium chloride, sodium citrate, citric acid, and methylcellulose; 15) the mixture can comprise triptorelin in an amount of about 0.01% weight per volume (as the acetate), methylparaben in an amount of about 0.09% weight per volume, propylparaben in an amount of about 0.01% weight per volume, sodium chloride in an amount of about 0.91% weight per volume, L-methionine in an amount of about 0.1% weight per volume, sodium citrate in an amount of about 0.186% weight per volume, citric acid in an amount of about 0.07% weight per volume, and methylcellulose in an amount of about 1.2% weight per volume; 16) the mixture can have a pH of about 5 to about 6; 17) the mixture in step b) can be mixed for a period of about 90 minutes to about 100 minutes; 18) the pH can be adjusted to about 5.3 to about 5.7 by the addition of aqueous citric acid solution; 19) the further mixing step d), can be carried out with cooling to 15° C. or below for a period of about 70 minutes to about 80 minutes; 20) the gonadotropin-releasing hormone can be at a concentration of about 50 µg/mL to about 200 µg/mL; 21) the process can provide triptorelin gel at a concentration of 100 µg triptorelin per mL (as triptorelin acetate).

DETAILED DESCRIPTION OF THE INVENTION

Figure 1:
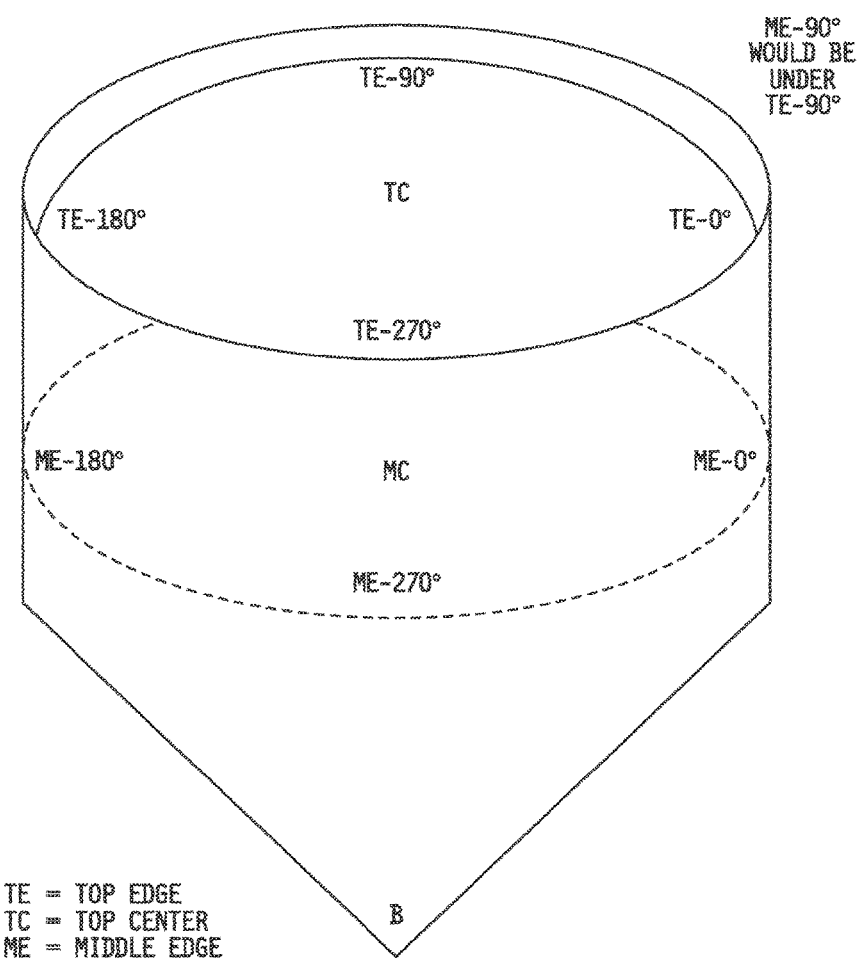
FIG. 1. Bulk Uniformity Sampling Locations in a holding vessel.

The following various embodiments are also provided in the following clauses.
1. A process for the manufacture of a gonadotropin releasing hormone containing gel from a primary compounding mixture batch of a drug product comprising the step of further mixing the primary compounding mixture batch using counter motion mixing (CMM).
2. The process of clause 1 wherein the gonadotropin releasing hormone has the formula or a solvate, a hydrate, or a pharmaceutically acceptable salt thereof, wherein
$R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;
$R^5$ is hydrogen or alkyl; and
X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.
3. The process according to clause 2 wherein the gonadotropin-releasing hormone is selected from the group consisting of compounds of the formula of clause 2 wherein
a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R;
b) $R^1$ is hydrogen, $R^2$ is hydrogen, X is $CH_2(CO)NH_2$; and $R^5$ is hydrogen;
c) $R^1$ is 1H-1-benzyl-imidazol-4-yl-methyl, $R^2$ is hydrogen, X is ethyl; and $R^5$ is hydrogen;
d) $R^1$ is 2-methylpropyl, $R^2$ is hydrogen, X is ethyl; and $R^5$ is hydrogen;
e) $R^1$ is 2-naphthylmethyl, $R^2$ is hydrogen, X is $CH_2(CO)NH_2$; and $R^5$ is hydrogen;
f) $R^1$ is t-butoxymethyl, $R^2$ is hydrogen, X is ethyl; $R^5$ is hydrogen; and the configuration of the carbon to which $R^1$ is attached is R;
g) $R^1$ is benzyl, $R^2$ is hydrogen, X is $CH_2(CO)NH_2$; $R^5$ is hydrogen; and the configuration of the carbon to which $R^1$ is attached is R;
h) $R^1$ is t-butoxymethyl, $R^2$ is hydrogen, X is $HN(CO)NH_2$; and $R^5$ is hydrogen;
i) $R^1$ is 1H-indol-3-yl-methyl, $R^2$ is hydrogen, X is ethyl; and $R^5$ is hydrogen;
j) $R^1$ is methyl, $R^2$ is hydrogen, X is hydrogen; $R^5$ is hydrogen; and the configuration of the carbon to which $R^1$ is attached is R;

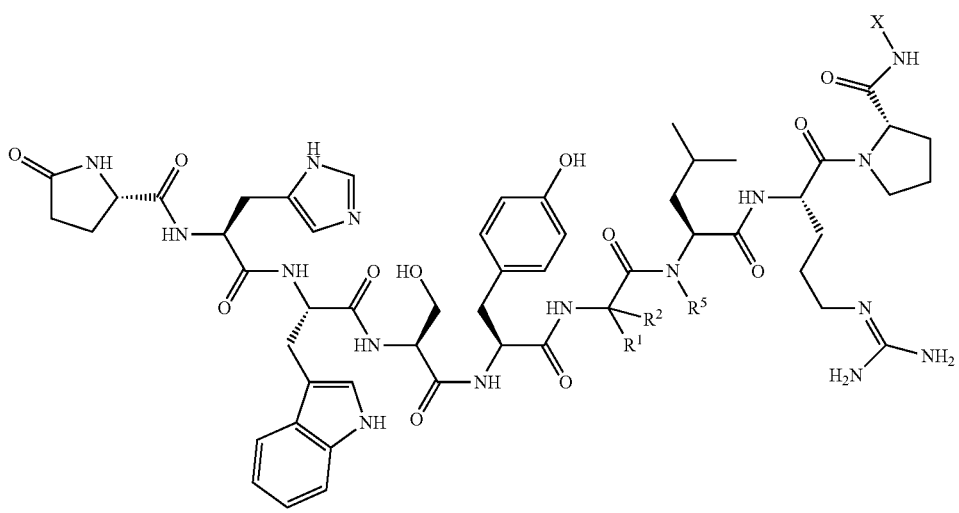

k) $R^1$ is 1H-indol-3-yl-methyl, $R^2$ is hydrogen, X is ethyl; $R^5$ is methyl; and the configuration of the carbon to which $R^1$ is attached is R;

l) $R^1$ is methyl, $R^2$ is hydrogen, X is $CH_2(CO)NH_2$; $R^5$ is hydrogen; and the configuration of the carbon to which $R^1$ is attached is R;

m) $R^1$ is 4-aminobutyl, $R^2$ is hydrogen, X is $HN(CO)NH_2$; $R^5$ is hydrogen; and the configuration of the carbon to which $R^1$ is attached is R;

n) $R^1$ is methyl, $R^2$ is methyl, X is $HN(CO)NH_2$; and $R^5$ is hydrogen; and o) $R^1$ is ethyl, $R^2$ is hydrogen, X is hydrogen; $R^5$ is hydrogen; and the configuration of the carbon to which $R^1$ is attached is R.

4. The process according to clause 1 wherein the gonadotropin-releasing hormone is triptorelin.

5. The process according to any one of clauses 1-4 wherein the hormone is in acetate form.

6. The process of any one of clauses 1-5 wherein the mixture comprises a preservative wherein the preservative is selected from the group consisting of methylparaben and propylparaben.

7. The process of any one of clauses 1-6 wherein the mixture comprises a stabilizer wherein the stabilizer is L-methionine.

8. The process of any one of clauses 1-7 wherein the mixture comprises a tonicity agent wherein the tonicity agent is sodium chloride.

9. The process of any one of clauses 1-8 wherein the mixture comprises a buffering agent wherein the buffering agent is sodium citrate-citric acid.

10. The process of any one of clauses 1-9 wherein the gelling agent is a polysaccharide selected from the group consisting of celluloses, dextrans, and alginates.

11. The process of clause 10 wherein the gelling agent is a cellulose and the cellulose is methylcellulose.

12. The process of clause 11 wherein the mixture comprises about 0.5 weight % to about 4.0 weight % of methylcellulose.

12.1. The process of clause 11 wherein the mixture comprises about 1 weight % to about 1.4 weight % of methylcellulose.

13. The process of clause 12 wherein the mixture comprises about 1.2 weight % of methylcellulose.

14. The process of any one of clauses 1-5 wherein the mixture comprises triptorelin, methylparaben, propylparaben, L-methionine, sodium chloride, sodium citrate, citric acid, and methylcellulose.

15. The process of clause 14 wherein the mixture comprises triptorelin in an amount of about 0.01% weight per volume (as the acetate), methylparaben in an amount of about 0.09% weight per volume, propylparaben in an amount of about 0.01% weight per volume, sodium chloride in an amount of about 0.91% weight per volume, L-methionine in an amount of about 0.1% weight per volume, sodium citrate in an amount of about 0.186% weight per volume, citric acid in an amount of about 0.07% weight per volume, and methylcellulose in an amount of about 1.2% weight per volume.

16. The process of any one of clauses 1-15 wherein the mixture has a pH of about 5 to about 6.

17. The process of any one of clauses 1-16 wherein the gonadotropin-releasing hormone is at a concentration of about 50 μg/mL to about 200 μg/mL.

18. The process of any one of clauses 1-17 wherein the process provides triptorelin gel at a concentration of 100 μg triptorelin per mL (as triptorelin acetate).

19. The process of any one of clauses 1-18, wherein the methycellulose is present in an amount that provides a viscosity of about 250 cP to about 400 cP.

20. The process of any one of clauses 1-19 comprising mixing the mixture using CMM for a period of about 90 minutes to about 100 minutes.

21. The process of any one of clauses 1-20 wherein the mixing of the mixture using CMM is carried out at about 15 RPM.

22. The process of any one of clauses 1-21, wherein the mixing of the mixture using CMM is carried out under passive vacuum.

23. The process of any one of clauses 1-22 comprising the further step of mixing of the mixture using CMM with cooling to 15° C. or below.

23a. The process of clause 23 wherein the mixing with cooling is carried out for a period of at least about 70 minutes.

24. The process of clause 23 wherein the mixing with cooling is carried out for a period of about 70 minutes to about 80 minutes.

25. The process of clause 23, 23a or 24 wherein the mixing using CMM with cooling is carried out at about 15 RPM.

26. The process of any one of clauses 23-25, wherein the mixing using CMM with cooling is carried out under passive vacuum.

27. The process of any one of clauses 1-26 comprising the further step of holding the mixture at least about 24 hours at 2-8° C.

101. A process for the manufacture of a gonadotropin releasing hormone containing gel comprising the steps of:
a) providing a primary compounding mixture batch of a drug product comprising the gonadotropin releasing hormone in an aqueous mixture further comprising:
optionally, a preservative;
optionally, a stabilizer;
optionally, a tonicity agent;
optionally, a buffering agent; and
a gelling agent;
b) further mixing the mixture using counter motion mixing (CMM);
c) optionally, adjusting the pH of the mixture;
d) further mixing the mixture using counter motion mixing (CMM) with cooling to 15° C. or below;
e) optionally, filtering the mixture, and;
f) holding the mixture at least 24 hours at 2-8° C. 102. The process of clause 101 wherein the gonadotropin releasing hormone has the formula

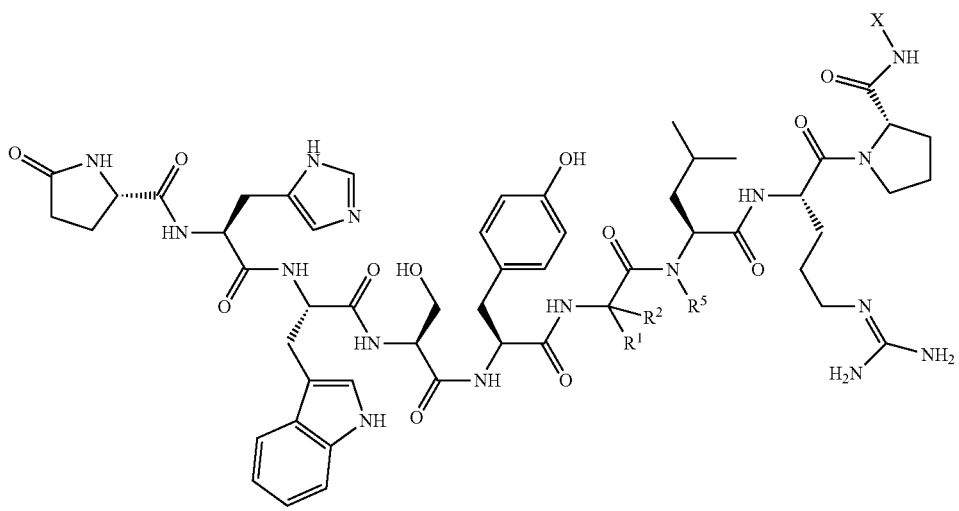

or a solvate, a hydrate, or a pharmaceutically acceptable salt thereof, wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;

$R^5$ is hydrogen or alkyl; and

X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

103. The process according to clause 102 wherein the gonadotropin-releasing hormone is selected from the group consisting of compounds of the formula of clause 102 wherein a) $R^1$ is 1H-indol-3-yl-methyl, $R^2$ is hydrogen, X is $CH_2(CO)NH_2$; $R^5$ is hydrogen; and the configuration of the carbon to which $R^1$ is attached is R;

b) $R^1$ is hydrogen, $R^2$ is hydrogen, X is $CH_2(CO)NH_2$; and $R^5$ is hydrogen;

c) $R^1$ is 1H-1-benzyl-imidazol-4-yl-methyl, $R^2$ is hydrogen, X is ethyl; and $R^5$ is hydrogen;

d) $R^1$ is 2-methylpropyl, $R^2$ is hydrogen, X is ethyl; and $R^5$ is hydrogen;

e) $R^1$ is 2-naphthylmethyl, $R^2$ is hydrogen, X is $CH_2(CO)NH_2$; and $R^5$ is hydrogen;

f) $R^1$ is t-butoxymethyl, $R^2$ is hydrogen, X is ethyl; $R^5$ is hydrogen; and the configuration of the carbon to which $R^1$ is attached is R;

g) $R^1$ is benzyl, $R^2$ is hydrogen, X is $CH_2(CO)NH_2$; $R^5$ is hydrogen; and the configuration of the carbon to which $R^1$ is attached is R;

h) $R^1$ is t-butoxymethyl, $R^2$ is hydrogen, X is $HN(CO)NH_2$; and $R^5$ is hydrogen;

i) $R^1$ is 1H-indol-3-yl-methyl, $R^2$ is hydrogen, X is ethyl; and $R^5$ is hydrogen;

j) $R^1$ is methyl, $R^2$ is hydrogen, X is hydrogen; $R^5$ is hydrogen; and the configuration of the carbon to which $R^1$ is attached is R;

k) $R^1$ is 1H-indol-3-yl-methyl, $R^2$ is hydrogen, X is ethyl; $R^5$ is methyl; and the configuration of the carbon to which $R^1$ is attached is R;

l) $R^1$ is methyl, $R^2$ is hydrogen, X is $CH_2(CO)NH_2$; $R^5$ is hydrogen; and the configuration of the carbon to which $R^1$ is attached is R;

m) $R^1$ is 4-aminobutyl, $R^2$ is hydrogen, X is $HN(CO)NH_2$; $R^5$ is hydrogen; and the configuration of the carbon to which $R^1$ is attached is R;

n) $R^1$ is methyl, $R^2$ is methyl, X is $HN(CO)NH_2$; and $R^5$ is hydrogen; and o) $R^1$ is ethyl, $R^2$ is hydrogen, X is hydrogen; $R^5$ is hydrogen; and the configuration of the carbon to which $R^1$ is attached is R.

104. The process according to clause 101 wherein the gonadotropin-releasing hormone is triptorelin.

105. The process according to any one of clauses 101-104 wherein the hormone is in acetate form.

106. The process of any one of clauses 101-105 wherein the mixture comprises a preservative wherein the preservative is selected from the group consisting of methylparaben and propylparaben.

107. The process of any one of clauses 101-106 wherein the mixture comprises a stabilizer wherein the stabilizer is L-methionine.

108. The process of any one of clauses 101-107 wherein the mixture comprises a tonicity agent wherein the tonicity agent is sodium chloride.

109. The process of any one of clauses 101-108 wherein the mixture comprises a buffering agent wherein the buffering agent is sodium citrate-citric acid.

110. The process of any one of clauses 101-109 wherein the gelling agent is a polysaccharide selected from the group consisting of celluloses, dextrans, and alginates.

111. The process of clause 110 wherein the gelling agent is a cellulose and the cellulose is methylcellulose.

112. The process of clause 111 wherein the mixture comprises about 0.5 weight % to about 4.0 weight % of methylcellulose.

112.1. The process of clause 111 wherein the mixture comprises about 1 weight % to about 1.4 weight % of methylcellulose.

113. The process of clause 112 wherein the mixture comprises about 1.2 weight % of methylcellulose.

114. The process of any one of clauses 101-105 wherein the mixture comprises triptorelin, methylparaben, propylparaben, L-methionine, sodium chloride, sodium citrate, citric acid, and methylcellulose.

115. The process of clause 114 wherein the mixture comprises triptorelin in an amount of about 0.01% weight per volume (as the acetate), methylparaben in an amount of about 0.09% weight per volume, propylparaben in an amount of about 0.01% weight per volume, sodium chloride in an amount of about 0.91% weight per volume, L-methionine in an amount of about 0.1% weight per volume, sodium citrate in an amount of about 0.186% weight per volume, citric acid in an amount of about 0.07% weight per volume, and methylcellulose in an amount of about 1.2% weight per volume.

116. The process of any one of clauses 101-115 wherein the mixture has a pH of about 5 to about 6.

117. The process of any one of clauses 101-116 comprising mixing the mixture in step b) for a period of about 90 minutes to about 100 minutes.

118. The process of any one of clauses 101-117 comprising step c) wherein the pH is adjusted to 5.3 to 5.7 by the addition of aqueous citric acid solution.

119. The process of any one of clauses 101-118 wherein the further mixing step d), with cooling to 15° C. or below, is carried out for a period of about 70 minutes to about 80 minutes.

120. The process of any one of clauses 101-119 wherein the gonadotropin-releasing hormone is at a concentration of about 50 µg/mL to about 200 µg/mL.

121. The process of any one of clauses 101-119 wherein the process provides triptorelin gel at a concentration of 100 µg triptorelin per mL (as triptorelin acetate).

122. The process of any one of clauses 101-121, wherein the methycellulose is present in an amount that provides a viscosity of about 250 cP to about 400 cP.

123. The process of any one of clauses 101-122, wherein the mixing of the mixture is carried out under passive vacuum.

124. The process of any one of clauses 101-123 wherein the mixing of the mixture is carried out using low shear mixing, for example using a counter motion mixer, for example at 15 RPM.

125. The process of any one of clauses 1-124 wherein the mixture is filtered using a 60 mesh screen.

126. The process of any one of clauses 1-125 wherein the primary compounding mixture batch of the drug product is transferred to the vessel for the final compounding phase using a pump, for example using a low shear, rotating lobe transfer pump.

127. The process of any one of clauses 1-126 wherein the final compounding phase batch of the drug product is transferred to the vessel for the final holding phase using a pump, for example using a low shear, rotating lobe transfer pump.

DETAILED DESCRIPTION OF THE ILLUSTRATIVE EMBODIMENTS

In one embodiment, a process for the manufacture of a GnRH-containing gel is described. The process comprises the steps of: a) providing a primary compounding mixture batch of a drug product comprising the gonadotropin releasing hormone in an aqueous mixture, further comprising: optionally, a preservative; optionally, a stabilizer; optionally, a tonicity agent; optionally, a buffering agent; and a gelling agent; b) further mixing the mixture; c) optionally, adjusting the pH of the mixture; d) further mixing the mixture with cooling to 15° C. or below; e) optionally, filtering the mixture, and; 0 holding the mixture at least 24 hours at 2-8° C.

All of the illustrative embodiments, modifications, and alternative forms described below may be applied to the embodiments described in the preceding paragraph of this Detailed Description section and to the embodiments described in the Summary of Invention.

In any embodiment described herein, the GnRH-containing gel composition can comprise: a) a hormone; and b) a pharmaceutically acceptable pH buffering agent to provide a pH in the range of about pH 4 to about pH 9. The pH of the composition herein described can range from about 4 to about 9. In other embodiments, the pH can range from about 4 to about 8, from about 4 to about 7, from about 4.5 to about 6.5, about 4.5 to about 6, from about 5 to about 6, or from about 5.3 to 5.7.

Further, the mixture can be produced, in accordance with the dosage form, through a method by appropriately mixing with, diluting with, or dissolving in an additive such as various excipients, disintegrants, binders, salts, lubricants, local anesthetics (e.g., lidocaine), diluents, preservatives, chelating agents, buffers, tonicity agents, antiseptic agents, wetting agents, emulsifiers, dispersants, stabilizers, a solution adjuvant, or combinations thereof.

Illustratively, the GnRH-containing gel can have, for example, a viscosity of about 10 (centipoise) cP to about 300,000 cP. In various illustrative embodiments, the viscosity can be about 100 cP to about 100,000 cP, about 250 cP to about 400 cP, about 300 cP to about 400 cP, about 500 cP to about 100,000 cP, about 700 cP to about 100,000 cP, about 200 cP to about 20,000 cP, about 200 cP to about 10,000 cP, about 200 cP to about 5,000 cP, about 200 to about 1,000 cP, about 200 cP to about 600 cP, about 100 cP to about 600 cP, about 100 cP to about 500 cP, about 200 cP to about 500 cP, about 200 cP to about 450 cP, or about 100,000 cP to about 250,000 cP. In accordance with various embodiments herein described, the viscosity can be about 200 cP, about 250 cP, about 300 cP, about 400 cP, about 500 cP, about 1,000 cP, about 15,000 cP, about 20,000 cP, about 30,000 cP, about 40,000 cP, about 50,000 cP, about 75,000 cP, about 100,000 cP, about 200,000 cP, or about 300,000 cP. The viscosity of a solution can be measured using a viscometer, such as a rheometer, based on techniques well-known in the art.

Typically, the GnRH-containing gel composition as described herein can comprise about 0.001 to about 3.0% weight/weight (w/w) of the GnRH or a salt thereof, more typically about 0.5-5.0% (w/w) or about 0.1-5.0% (w/w) of the GnRH or a salt thereof, a preservative, a gelling agent (i.e., a viscosity-modifying agent), a buffering agent to maintain a pH between about 5 to about 6, and a tonicity agent to maintain a tonicity between about 200 to about 400 mOsm/kG.

In accordance with any embodiment described herein, the GnRH-containing gel composition is sufficiently viscous that the composition stays adhered to the target tissue for a sufficient time to deliver an effective amount of the GnRH, and/or the GnRH-containing gel composition may be effective because the viscosity of the GnRH-containing gel composition is similar to intracellular viscosity. The typical viscosity will depend on factors such as, for example, the rate of penetration of the GnRH and the quantity of the hormone that is applied. Suitable gelling agents include but are not limited to, ionic and non-ionic water soluble polymers; crosslinked acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof.

The gelling agent may be in the form of a gel, paste, cream, ointment, and the like. In one embodiment, the GnRH-containing gel composition comprises a hormone and a gel, as a viscosity modifying agent. In one embodiment, the gel is a hydrogel, a lipogel, or a viscous sol. In another embodiment, the gel is a hydrogel. The gel may be prepared using any method known in the art, for example, such as those methods described in U.S. Pat. Nos. 6,908,623 and 7,456,207, incorporated herein by reference. Particularly, the gel may be prepared as described herein.

In any embodiment described herein, the gelling agent (i.e., a viscosity modifying agent) comprises a polysaccharide. In accordance with the compositions herein described, the polysaccharide may include, for example, alginates and glucose, such as glycogens, starches (e.g., amylose and amylopectin), celluloses, and dextrans. The polysaccharide can be, for example, a methyl, ethyl, or propyl cellulose ester, ether, hydroxy-ether, hydroxy-alkyl, or hydroxy-ester. To achieve the desired viscosity, a sufficient amount of one or more polysaccharides may be used. Typically, about 0.25 to about 10 weight % polysaccharide (based on the total weight of the composition) is desirable. In another embodiment, the weight % of the polysaccharide is about 0.25 weight % to about 3.0 weight %, about 1.0 weight % to about 7 weight %, about 1.0 weight % to about 4.0 weight %, or about 1.0 weight % to about 2.0 weight %. In other embodiments, the weight % of the polysaccharide is about 0.1%, about 0.5%, about 0.75%, about 0.8%, about 0.9%, about 1.0%, about 1.1%, about 1.2%, about 1.4%, about 1.8%, about 2.0%, about 5%, about 8%, or about 10% (all in weight/weight). To increase the viscosity of the composition, the polysaccharide may be used in conjunction with one or more non-polysaccharide viscosifiers known in the art. Examples of possible non-polysaccharide viscosifiers that could be used in conjunction with one or more polysaccharides include xantham gum, alginic acids and salts thereof, magnesium aluminum silicate, dextrins, sucrose and derivatives thereof, and mixtures thereof. The amount of non-polysaccharide viscosifier, if present, can be about 0.1 weight % to about 10 weight %, depending on the desired viscosity.

In any embodiment described herein, the gelling agent comprises a cellulose. Illustrative embodiments of the cellulose, as herein described, include methylcellulose, ethylcellulose, hydroxypropyl cellulose, carbomethyl cellulose, hydroxypropyl methyl cellulose, and hydroxyethyl methyl cellulose. The cellulose can be a cellulose derivative, preferably a non-ionic cellulose ester, ether, hydroxy-ether, or hydroxy-ester, or a non-ionic starch derivative. Typically, about 0.25 weight % to about 10 weight % of the cellulose (based on the total weight of the composition) is desirable. In another embodiment, the weight % of the cellulose is about 0.25 weight % to about 3.0 weight %, about 0.5 weight % to about 3.0 weight %, about 0.5 weight % to about 4.0 weight %, about 1.0 weight % to about 7 weight %, about 1.0 weight % to about 4.0 weight %, or about 1.0 weight % to about 2.0 weight %. In other embodiments, the weight % of the cellulose is about 0.1%, about 0.5%, about 0.75%, about 0.8%, about 0.9%, about 1.0%, about 1.1%, about 1.2%, about 1.4%, about 1.8%, about 2.0%, about 5%, about 8%, or about 10% (all in weight/weight). If a uniform gel is desired, dispersing agents such as alcohol, sorbitol, or glycerin can be added, or the gelling agent can be dispersed by tituration, mechanical mixing, or stirring, or combinations thereof.

Acceptable stabilizers for use in the described compositions include, an L-amino acid and an L-methionine. In other embodiments, stabilizers that can be used include, but are not limited to, polysaccharides such as acacia, agar, alginic acid, guar gum and tragacanth, gelatin and synthetic and semi-synthetic polymers such as carbomer resins, cellulose ethers, and carboxymethyl chitin. The stabilizer is generally in an amount of about 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume). In one embodiment, in the presence of a stabilizer as herein described, the shelf life of the composition can be at least 12 months, at least 18 months, or at least 24 months. In another embodiment, the composition can be stored at temperatures ranging from about 2° C. to about 8° C. Inert carriers can also be included such as lactose, starch, dextrin, dicalcium phosphate, and calcium sulfate. In one embodiment including a stabilizer, the composition is chemically stable and remains at least 99% pure, at least 99.5% pure, or at least 99.7% pure, for at least three months.

The tonicity agent can be non-ionic or ionic. Illustratively, acceptable tonicity agents for use in the described methods and compositions include, for example, ionic agents such as sodium chloride, potassium chloride, or a balanced salt solution. In accordance with one embodiment, the tonicity agent is present in an amount to achieve a tonicity between about 200-400 mOsm/kG, about 220-380 mOsm/kG, or about 250-340 mOsm/kG. Non-ionic tonicity agents include diols, such as glycerol, mannitol, erythritol, polyethylene glycol, propylene glycol; and sugars such as sucrose and dextrose. The tonicity agent is generally in an amount of about 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, 0.5 to about 2.0%, about 0.6 to about 2.0%, about 0.5 to about 1.8%, about 0.6 to about 1.8%, about 1.0 to about 5.0%, about 1.0 to about 10%, or about 1.0 to about 20% (all in weight/volume).

In any embodiment described herein, the buffering agents for use in the compositions herein described are those agents known to the skilled artisan to be pH buffering agents or compositions and include, for example, acetate, borate, carbonate, citrate, and phosphate buffers, as well as various biological buffers, for example, TAPS, Bicine, Tris, Tricine, HEPES, TES, MOPS, PIPES, Cacodylate, and MES. Other buffering agents include hydrochloric acid, sodium hydroxide, magnesium oxide, monopotassium phosphate, bicarbonate, ammonia, carbonic acid, sodium citrate, citric acid, acetic acid, disodium hydrogen phosphate, borax, boric acid, and the like. The buffering agent is generally in an amount of about 0.01 to about 10%, about 0.02 to about 10%, about 0.02 to about 5%, about 0.02 to about 2.0%, about 0.02 to about 1.0%, about 0.02 to about 0.5%, about 0.05 to about 10.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

The buffering agent used in the GnRH-containing gel composition herein described can be used at any concentration needed to obtain the desired pH range. For example, the buffering agent can be used at a concentration of about 0.001M to about 1M, about 0.001M to about 2M, about 0.001M to about 5M, about 0.05M to about 0.1M, about 0.05M to about 0.2M, about 0.05M to about 1M, 0.05M to about 2M, about 0.05 to about 5M, about 0.1M to about 1M, about 0.1M to about 2M, about 0.1M to about 5M. Any amount of buffering agent needed to obtain the desired pH range can be used in the formulations described herein. Typically, the pharmaceutically acceptable buffering agent can be used to provide a pH in the range of about pH 4 to about pH 9. The pH of the composition herein described can range from about 3 to about 10, or about 4 to about 9. In any embodiment described herein, the pH can range from about 4 to about 8, from about 4 to about 7, from about 4.5 to about 6.5, about 4.5 to about 6, from about 5 to about 6, about 5 to about 5.5, about 4 to about 6, about 4.5 to about 5.5, or about 5.3 to 5.7.

In any embodiment described herein, the GnRH-containing gel composition herein described comprises one or more pharmaceutically acceptable preservatives. As used herein, the term "preservative" includes an agent or a combination of agents that aids in stabilizing the composition, inhibiting microbial growth, or both. Examples of suitable preservatives include parabens (e.g., methyl, ethyl, propyl, and butyl esters of parahydroxybenzoic acid), propyl gallate, sorbic acid and its sodium and potassium salts, propionic acid and its calcium and sodium salts, "Dioxin" (6-acetoxy-2,4-dimethyl-m-dioxane), "Bronopol" (2-bromo-2-nitropropane-1, 3-diol) and salicylanilides such as disbromosalicylanilide, tribromosalicylamilides, "Cinaryl" 100 and 200 or "Dowicil" 100 and 200 (Cis isomer of 1-(3-chloroallyl-3,5,7-triaza-1-azanidadamantane chloride), hexachlorophene, sodium benzoate, citric acid, ethylene diaminetetraacetic acid and its alkali metal and alkaline earth metal salts, butyl hydroxyanisol, butyl hydroxytoluene, phenolic compounds such as chloro- and bromocresols and chloro- and bromo-oxylenols, quaternary ammonium compounds like benzalkonium chloride, aromatic alcohols such as phenylethyl alcohol, benzyl alcohol, etc., chlorobutanol, quinoline derivatives such as iodochlorohydroxyquinolin, and the like. The total amount of preservative, when present, is about 0.005 weight % to about 2 weight %, about 0.001 weight % to 1.0 weight %, about 0.005 weight % to about 0.25 weight %, or about 0.05 weight % to about 0.2 weight %, typically about 0.01 weight % to about 0.1 weight % (all in weight/weight).

In any embodiment described herein, the GnRH-containing gel composition can comprise a chelating agent, such as those known to those skilled in the art, for example, ethylenediamine tetraacetate (EDTA), diethylenetriaminepentaacetic acid (DTPA), and N,N-bis(carboxymethyl)glycine (NTA), or salts thereof. The GnRH-containing gel composition can contain about 0.003 weight % to about 1.0 weight %, about 0.02 weight % to about 0.2 weight %, about 0.01 weight % to about 1.0 weight %, or about 0.02 weight % to about 0.5 weight % (all in weight/volume) of the chelating agent.

In any embodiment described herein, antimicrobial agents can be included in the GnRH-containing gel composition described herein. Such agents may include, but are not limited to 5-chloro-2-(2,4-dichlorophenoxy)-phenol, 8-hydroxyquinoline, copper II compounds, phthalic acid, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride, octenidine, iodine, sulfonamides, bisbiguanides, phenolics, delmopinol, octapinol, and other piperidino derivatives, and nicin preparations, any suitable antibiotics such as augmentin, amoxicillin, tetracycline, doxycycline, minocycline, metronidazole, neomycin, kanamycin, and clindamycin, and any salts of any of these compounds where applicable, and any combinations of these compounds. In yet another embodiment, anti-fungal compounds can be included, alone or in combination with any of the above-described antimicrobials. Anti-fungals agents that are suitable for use in the GnRH-containing gel composition described herein include, but are not limited to, nystatin, miconazole, econazole nitrate, clotrimazole, and flucytosine. The antimicrobial or anti-fungal agents can be added to the formulations herein described in an amount of about 0.01 to about 10%, about 0.01 to about 5%, about 0.01 to about 2.0%, about 0.01 to about 1.0%, about 0.01 to about 0.5%, about 0.01 to about 0.2%, 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

In any embodiment described herein, antioxidants can also be added to the GnRH-containing gel composition. For example, antioxidants used herein can include beta-carotene, vitamin E, vitamin C, vitamin A, tocopherol, butylated hydroxytoluene, butylated hydroxyanisole, tertiary-butylhydroquinone, propyl gallate, ascorbic acid, sodium metabisulfite, uric acid, carotenoids, flavonoids, melatonin, and ethoxyquin. The antioxidants can be added to the formulations herein described in an amount of about 0.01 to about 10%, about 0.01 to about 5%, about 0.01 to about 2.0%, about 0.01 to about 1.0%, about 0.01 to about 0.5%, about 0.01 to about 0.2%, 0.05 to about 10%, about 0.05 to about 5%, about 0.05 to about 2.0%, about 0.05 to about 1.0%, about 0.05 to about 0.5%, about 0.05 to about 0.2%, about 0.1 to about 5%, about 0.1 to about 10%, about 0.1 to about 20%, about 1 to about 5%, about 1 to about 10%, about 1 to about 20% (all in weight/volume).

The GnRH-containing gel compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

As described herein, the GnRH-containing gel composition contains a gonadotropin releasing hormone, or a derivative or analog thereof, and combinations thereof, in an amount effective to synchronize the time of insemination in a swine without heat detection. The hormone can be in acetate form. Further, the hormone can be a gonadotropin-releasing hormone. As used herein, "gonadotropin-releasing hormone" (GnRH) refers to any gonadotropin releasing hormone, including gonadotropin releasing hormone analogs and derivatives, and gonadotropin releasing hormone agonists. In one embodiment, the gonadotropin releasing hormone can be synthetic. In another embodiment, the gonadotropin-releasing hormone can be pGlu-His-Trp-Ser-Tyr-Gly-Leu-Arg-Pro-GlyNH$_2$ (see, for example, U.S. Pat. No. 5,688,506, incorporated herein by reference) or triptorelin.

Examples of gonadotropin releasing hormones for use herein include, but are not limited to, leuprolide, nafarelin, buserelin, [DAla$^6$, des Gly-NH$_2$$^{10}$]GnRH, [DLys$^6$]GnRH, [DAla$^6$]GnRH, [2-Me-Ala$^6$]GnRH, [D-α-aminobutyroyl$^6$, des-GlyNH$_2$$^{10}$]GnRH, triptorelin, lutrelin, goserelin, deslorelin, and histrelin. Generally, gonadotropin releasing hormones are modeled after the natural gonadotropin releasing hormone decapeptide with specific amino acid substitutions typically at positions 6 and 10. Triptorelin is an example of a gonadotropin releasing hormone with only a single substitution at position 6.

In any embodiment described herein, a gonadotropin-releasing hormone of formula (I) can be used In another embodiment, the gonadotropin-releasing hormone is a hormone of formula I where $R^1$ is 1H-indol-3-yl-methyl, $R^2$ is hydrogen, X is $CH_2(CO)NH_2$; $R^5$ is hydrogen; and the configuration of the carbon to which $R^1$ is attached is R.

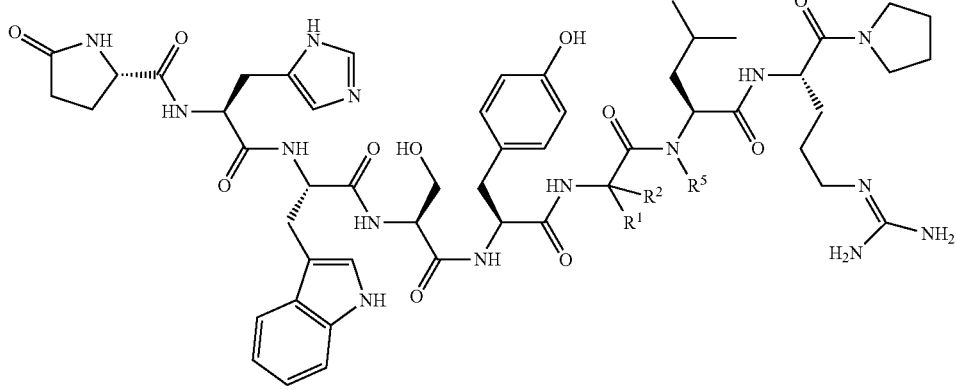

(I)

or a solvate, a hydrate, or a pharmaceutically acceptable salt thereof wherein $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;

$R^5$ is hydrogen or alkyl; and

X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

In another embodiment, $R^1$ is a methylene-aryl. In another embodiment, the aryl is phenyl or 4-hydroxyphenyl. In another embodiment, $R^1$ is a methylene-heteroaryl. In yet another embodiment, the heteroaryl is selected from the group consisting of pyridyl, thiazolyl, pyridazolyl, pyrimidinyl, quinolinyl, pyrazolyl, imidazolyl, pyrrolyl, indolyl, benzopyrazolyl, and benzimidazolyl; and $R^2$ is hydrogen or methyl. In various other embodiments, $R^1$ is 2-methylpropyl, $R^1$ is 2-naphthylmethyl, $R^1$ is t-butoxymethyl, $R^1$ is methyl, $R^1$ is 4-aminobutyl, $R^1$ is ethyl, $R^1$ and $R^2$ are methyl, $R^1$ is 1H-indol-3-yl-methyl, $R^1$ is 1H-1-benzyl-imidazol-4-yl-methyl, or $R^1$ is benzyl.

In additional embodiments, $R^2$ is hydrogen, $R^2$ is hydrogen and the gonadotropin-releasing hormone has the R-configuration at the carbon to which $R^1$ is attached, $R^2$ is hydrogen and the gonadotropin-releasing hormone has the S-configuration at the carbon to which $R^1$ is attached, or $R^2$ is hydrogen and the gonadotropin-releasing hormone is a mixture of gonadotropin-releasing hormones having the R-configuration at the carbon to which $R^1$ is attached and the S-configuration at the carbon to which $R^1$ is attached.

In still additional embodiments, X is $CH_2(CO)NH_2$, X is $HN(CO)NH_2$, X is ethyl, X is hydrogen, $R^5$ is hydrogen, or $R^5$ is methyl.

In another embodiment, the gonadotropin-releasing hormone is a hormone of formula I where $R^1$ is hydrogen, $R^2$ is hydrogen, X is $CH_2(CO)NH_2$; and $R^5$ is hydrogen.

In another embodiment, the gonadotropin-releasing hormone is a hormone of formula I where $R^1$ is 1H-1-benzyl-imidazol-4-yl-methyl, $R^2$ is hydrogen, X is ethyl; and $R^5$ is hydrogen.

In another embodiment, the gonadotropin-releasing hormone is a hormone of formula I where $R^1$ is 2-methylpropyl, $R^2$ is hydrogen, X is ethyl; and $R^5$ is hydrogen.

In yet another embodiment, any one of the previously described embodiments wherein X is $CH_2C(O)NH_2$ is provided.

In another embodiment, the gonadotropin-releasing hormone is a hormone of formula I where $R^1$ is 2-naphthlymethyl, $R^2$ is hydrogen, X is $CH_2(CO)NH_2$; and $R^5$ is hydrogen.

In another embodiment, the gonadotropin-releasing hormone is a hormone of formula I where $R^1$ is t-butoxymethyl, R2 is hydrogen, X is ethyl; $R^5$ is hydrogen; and the configuration of the carbon to which $R^1$ is attached is R.

In another embodiment, the gonadotropin-releasing hormone is a hormone of formula I where $R^1$ is benzyl, $R^2$ is hydrogen, X is $CH_2(CO)NH_2$; $R^5$ is hydrogen; and the configuration of the carbon to which $R^1$ is attached is R.

In another embodiment, the gonadotropin-releasing hormone is a hormone of formula I where $R^1$ is t-butoxymethyl, $R^2$ is hydrogen, X is $HN(CO)NH_2$; and $R^5$ is hydrogen.

In another embodiment, the gonadotropin-releasing hormone is a hormone of formula I where $R^1$ is 1H-indol-3-yl-methyl, $R^2$ is hydrogen, X is ethyl; and $R^5$ is hydrogen.

In another embodiment, the gonadotropin-releasing hormone is a hormone of formula I where $R^1$ is methyl, $R^2$ is hydrogen, X is hydrogen; $R^5$ is hydrogen; and the configuration of the carbon to which $R^1$ is attached is R.

In another embodiment, the gonadotropin-releasing hormone is a hormone of formula I where $R^1$ is 1H-indol-3-ylmethyl, $R^2$ is hydrogen, X is ethyl; $R^5$ is methyl; and the configuration of the carbon to which $R^1$ is attached is R.

In another embodiment, the gonadotropin-releasing hormone is a hormone of formula I where $R^1$ is methyl, $R^2$ is hydrogen, X is $CH_2(CO)NH_2$; $R^5$ is hydrogen; and the configuration of the carbon to which $R^1$ is attached is R.

The gonadotropin releasing hormones, and analogs thereof, such as the analogs described in the formula above, used herein can be administered in the form of pharmaceutically acceptable non-toxic salts or complexes. The salts include acid addition salts such as, for example, hydrochloride, hydrobromide, sulfate, phosphate, nitrate, oxalate, fumarate, gluconate, tannate, maleate, acetate, benzoate, succinate, alginate, malate, ascorbate, tartrate and the like. The complexes can be with metals such as for example zinc, barium, calcium, magnesium, aluminum and the like.

The amount of the GnRH effective for use in accordance with the methods and compositions described herein depends on many parameters, including the molecular weight of the hormone, its route of administration, and whether or not it is in its native form.

In one embodiment, the modifications to the process described herein include an additional mixing step as the final compounding process step with a counter motion mixer and cooling of the batch. In another embodiment, after all chemical components have been added and mixed in the primary compounding phase, the primary compounding batch is transferred to a vessel with counter motion mixing capability, mixed under passive vacuum, and then cooled with chilled water to 15° C. or below. In yet another illustrative aspect, the batch is stored in cold storage (2° C. to 8° C.) for at least 24 hours until ready for packaging.

In another embodiment, for a 500 kg batch, the final mixing step may be carried out in a round bottom, jacketed, stainless steel 1500 L pressure/vacuum kettle with counter motion mixer. In yet another embodiment, following the cooling with chilled water to 15° C. or below, the batch is then transferred to a round bottom, jacketed, stainless steel 700 L kettle as a final holding kettle for holding in cold storage (2° C. to 8° C.) for at least 24 hours until ready for packaging.

In yet another illustrative embodiment, for a 500 kg batch, for mixing the primary compounding phase which provides the primary compounding batch, the dispersator blade for a round bottom, jacketed, stainless steel 700 L kettle may be a 14-inch dispersator blade to more adequately mix the larger volume of product, and the paraben phase may be transferred to the final compounding phase using a pump due to the larger volume of product.

In another illustrative aspect, in the final compounding phase as described herein, the additional mixing and cooling provide adequate mixing and sufficient time to cool the batch and hydrate the methylcellulose due to the larger batch size. In another embodiment, the passive vacuum assists in deaerating the product. In another illustrative embodiment, the additional mixing and cooling have been shown to have no adverse effect on the identity, strength, quality, purity, or potency of the drug product as evidenced by the stability data for 500-kg batches manufactured with the modified process. As used herein, the passive vacuum is a pressure obtained when a vessel is evacuated to a specified set level, then the vacuum pump is turned off until or unless the vacuum level approaches a lower specification limit at which the pump is turned on to re-establish the set level of vacuum. The set level for the vacuum may be, for example, about 12 inches of mercury, with the lower specification limit, for example, about 0 inches of mercury.

In yet another embodiment, after manufacture the GnRH-containing gel compositions described can be packaged in a primary container, for example, a glass vial, such as an amber glass vial with a rubber stopper and/or an aluminum tear-off seal. In another embodiment, the primary container can be plastic or aluminum, and the primary container can be sealed. In another embodiment, the primary container may be contained within a secondary container to further protect the composition from light. The secondary container can be, for example, cardboard.

EXAMPLES

Example

A proposed manufacturing process for a GnRH-containing drug product is outlined in FIG. 1A. Processes at a smaller scale are described in WO 2010/124220 A1. In FIG. 1A, (**) indicates modification of a step. For certain values of the proposed process which are listed as "not defined" in Tables 1-4, see the values of Example 1, below.

Feasibility Example

500-Kg Drug Product Manufacturing Process

Using a manufacturing process similar to that outlined in FIG. 1A, a feasibility batch at commercial scale for triptorelin gel, 100 µg/mL, was prepared. The batch was transferred to storage in a stainless steel storage vessel. Preliminary (0-time) testing and testing after bulk hold at room temperature were performed on the batch with respect to the following specifications.

Viscosity (250-400 cps)

Triptorelin (90%-110% L, L=0.010% w/v) L=label claim

Methylparaben (sodium salt) (80%-120% F, F=0.089% w/v) F=formula

Propylparaben (sodium salt) (80%-120% F, F=0.010% w/v) F=formula

For uniformity testing, samples were pulled from the bulk container at the following locations, as shown in FIG. 1: TE 0°, TE 180°, TC, ME 0°, MC, and B.

At 0-time (initial time), results from the Top, Middle and Bottom sample locations were tested for viscosity and were within specification:

| Viscosity (250-400 cps) | |
|---|---|
| T | 385 |
| M | 356 |
| B | 345 |

Results for Triptorelin did not meet specification.

The feasibility batch was subjected to a bulk hold study at room temperature with the following results reported:

| | Viscosity | Triptorelin | Methylparaben | Propylparaben |
|---|---|---|---|---|
| Day 7 | | | | |
| T | 36 | 110 | 88 | 80 |
| M | >400 (off-scale) | 122 | 102 | 106 |
| B | >400 (off-scale) | 122 | 105 | 114 |

-continued

|  | Viscosity | Triptorelin | Methylparaben | Propylparaben |
|---|---|---|---|---|
| Day 14 | | | | |
| T | 27 | 108 | 88 | 80 |
| M | 208 | 117 | 96 | 95 |
| B | 554 | 129 | 106 | 106 |
| Day 21 | | | | |
| T | 24 | 106 | 89 | 81 |
| M | 265 | 114 | 97 | 97 |
| B | 453 | 118 | 104 | 109 |

The examples below include one or more of the following changes, reflected in FIG. 1B: In the primary compounding phase, the equipment is modified for a slight increase (from 12 inches to 14 inches) in the primary compounding phase. A transfer pump is used for addition of the paraben phase to the stirring mixture in the final compounding phase. The batch is cooled to 15° C. or below prior to transfer. After transfer the batch is held in cold storage for at least 24 hours.

Example 1

Description of a Modified Commercial 500-kg Drug Product Manufacturing Process

An improved (modified) manufacturing process for a GnRH-containing drug product as initially used to provide a placebo formulation is described. This process exemplifies the times and mix speeds for the "Proposed Process" omitted in Table 1 and Table 2, but adds the first CMM step of Table 3, in addition it provides the mixing speed for the Product Transfer to Holding step of Table 4.

This modified process is outlined in FIG. 1B through the pH Check Phase and in the Product Transfer to Holding. In FIG. 1B, (**) indicates modification of a step, and (*) indicates a new step. The paraben phase, primary compounding phase, final compounding phase, pH adjustment phase, and transfer/filter to holding phase are performed under lighting that blocks or does not emit UV-A, UV-B and UV-C wavelengths since the drug substance should be protected from light. Bulk product is protected from light and stored in a cold room after compounding and until needed for packaging. A description of the phases is provided below.

Paraben Phase: The Paraben Phase is prepared in a 700 L round bottom, jacketed, stainless steel kettle which is charged with approximately 245 kg of Purified Water USP/EP. This is placed under a 60 HP Dissolver with a 10 inch standard dissolver blade. The Phase is mixed at 420 RPM while adding Methylparaben Sodium Salt (445 g) and Propylparaben Sodium Salt (50.0 g). Mixing is continued for 5 minutes at 420 RPM. Sodium Chloride USP (4.51 kg) is added and mixing continued for 5 minutes at 450 RPM. To the batch, L-Methionine USP (495 g) is added and mixing continued for 5 minutes at 450 RPM. Sodium Citrate USP (920 g) is added and the Phase mixed for 10 minutes at 450 RPM.

Primary Compounding Phase: The Primary Compounding Phase is prepared in a 700 L round bottom, jacketed, stainless steel Kettle which is charged with 219 kg of Purified Water USP/EP. This is placed under a 60 HP Dissolver with a 14 inch dispersator blade. This is mixed at 383 RPM while adding Citric Acid USP (345 g). Mixing continues for 5 minutes at 383 RPM. Triptorelin Acetate is omitted for the placebo; otherwise approximately 50.0 g of Triptorelin Acetate (adjusted for potency) is added. This is followed with a Purified Water USP/EP (1000 g) rinse of the Triptotelin Acetate container. Mixing is continued for 10-20 minutes at 300-400 RPM. Using a 60 GPM transfer pump, the Paraben Phase is transferred into the Primary Compounding Phase. This is followed with a Purified Water USP/EP (7.50 kg) rinse. Mixing is continued for 5 minutes at 383 RPM. Approximately 6.00 kg Methylcellulose USP (adjusted for viscosity) is slowly added to the batch with mixing at 383 to 505 RPM. Mixing is continued for 15 minutes at 505 RPM.

Final Compounding Phase: The drug product is transferred to a 1500 L round bottom, jacketed, stainless steel pressure/vacuum kettle with Counter Motion Mixing (CMM) for the Final Compounding Phase. The batch is transferred into the final compounding kettle by passive vacuum. This is followed with a 10.0 kg Purified Water USP/EP rinse using passive vacuum while mixing CMM at 12 RPM. The batch is mixed under passive vacuum and with CMM at 15 RPM for 60-90 minutes. A sample is taken for an in-process pH check (specification range: 5.3-5.7). If no adjustment is necessary, 5.00 kg of Purified Water USP/EP is added to the batch, and mixing is continued for 70 minutes under passive vacuum, CMM at 15 RPM.

pH Check Phase: If the pH adjustment is necessary, the required amount of Citric Acid USP is dissolved in the 5.00 kg of Purified Water USP/EP above prior to addition to the batch.

Transfer/Holding: After batch reconciliation, the batch is transferred with CMM at 10 RPM and using a 60 GPM transfer pump with a 1-ft canister filter with a 60-mesh screen into a 700 L round bottom, stainless steel kettle. The bulk drug product is sampled and tested prior to filling.

Example 2

Description of the Modified Commercial 500-Kg Drug Product Manufacturing Process An improved (modified) manufacturing process for a GnRH-containing drug product is described. The modified process is outlined in FIG. 1B. Processes at a smaller scale are described in WO 2010/124220 A1. In FIG. 1B, (**) indicates modification of a step, and (*) indicates a new step. The paraben phase, primary compounding phase, final compounding phase, pH adjustment phase, and transfer/filter to holding phase are performed under lighting that blocks or does not emit UV-A, UV-B and UV-C wavelengths since the drug substance should be protected from light. Bulk product is protected from light and stored in a cold room after compounding and until needed for packaging. A description of the phases is provided below.

Paraben Phase:

The Paraben Phase is prepared in a 700 L round bottom, jacketed, stainless steel kettle which is charged with approximately 245 kg of Purified Water USP/EP. This is placed under a 60 HP Dissolver with a 10 inch standard dissolver blade. The Phase is mixed at 525-575 RPM while adding Methylparaben Sodium Salt (445 g) and Propylparaben Sodium Salt (50.0 g). Mixing is continued for 5-10 minutes at 525-575 RPM. Sodium Chloride USP (4.51 kg) is added and mixing continued for 10-15 minutes at 525-575 RPM. To the batch, L-Methionine USP (495 g) is added and mixing continued for 5-10 minutes at 525-575 RPM. Sodium Citrate USP (920 g) is added and the Phase mixed for 10-20 minutes at 525-575 RPM.

Primary Compounding Phase:

The Primary Compounding Phase is prepared in a 700 L round bottom, jacketed, stainless steel Kettle which is charged with 219 kg of Purified Water USP/EP. This is placed under a 60 HP Dissolver with a 14 inch dispersator blade. This is mixed at 300-400 RPM while adding Citric Acid USP (345 g). Mixing continues for 5-10 minutes at 300-400 RPM. Approximately 50.0 g of Triptorelin Acetate (adjusted for potency) is added. This is followed with a Purified Water USP/EP (1000 g) rinse of the Triptotelin Acetate container. Mixing is continued for 10-20 minutes at 300-400 RPM. Using a 60 GPM transfer pump, the Paraben Phase is transferred into the Primary Compounding Phase. This is followed with a Purified Water USP/EP (7.50 kg) rinse. Mixing is continued for 5-10 minutes at 300-400 RPM. Approximately 6.00 kg Methylcellulose USP (adjusted for viscosity) is slowly added to the batch. Mixing is continued for 30-60 minutes at 450-570 RPM.

Final Compounding Phase:

The drug product is transferred to a 1500 L round bottom, jacketed, stainless steel pressure/vacuum kettle with Counter Motion Mixing (CMM) for the Final Compounding Phase. The batch is transferred into the final compounding kettle by passive vacuum. This is followed with a 10.0 kg Purified Water USP/EP rinse using passive vacuum while mixing CMM at 12 RPM. The batch is mixed under passive vacuum and with CMM at 15 RPM for 90-100 minutes. A sample is taken for an in-process pH check (specification range: 5.3-5.7). If no adjustment is necessary, 5.00 kg of Purified Water USP/EP is added to the batch and mixing is continued for 70-80 minutes under passive vacuum, CMM at 15 RPM and cooling with chilled water to 15° C. or below.

pH Check Phase:

If the pH adjustment is necessary, the required amount of Citric Acid USP is dissolved in the 5.00 kg of Purified Water USP/EP above prior to addition to the batch. Once cooling is complete, if the pH adjustment has been necessary, a sample is pulled for a final pH check.

Transfer/Holding:

After batch reconciliation, the batch is transferred with CMM at 10 RPM and using a 60 GPM transfer pump with a 1-ft canister filter with a 60-mesh screen into a 700 L round bottom, stainless steel kettle. This is stored in the cold room for at least 24 hours prior to sampling for preliminary testing. A sample is collected from each of the top, middle and bottom of the holding kettle for testing. Samples and batch are returned to the cold room. The bulk drug product is sampled and tested prior to filling.

Figure 2:
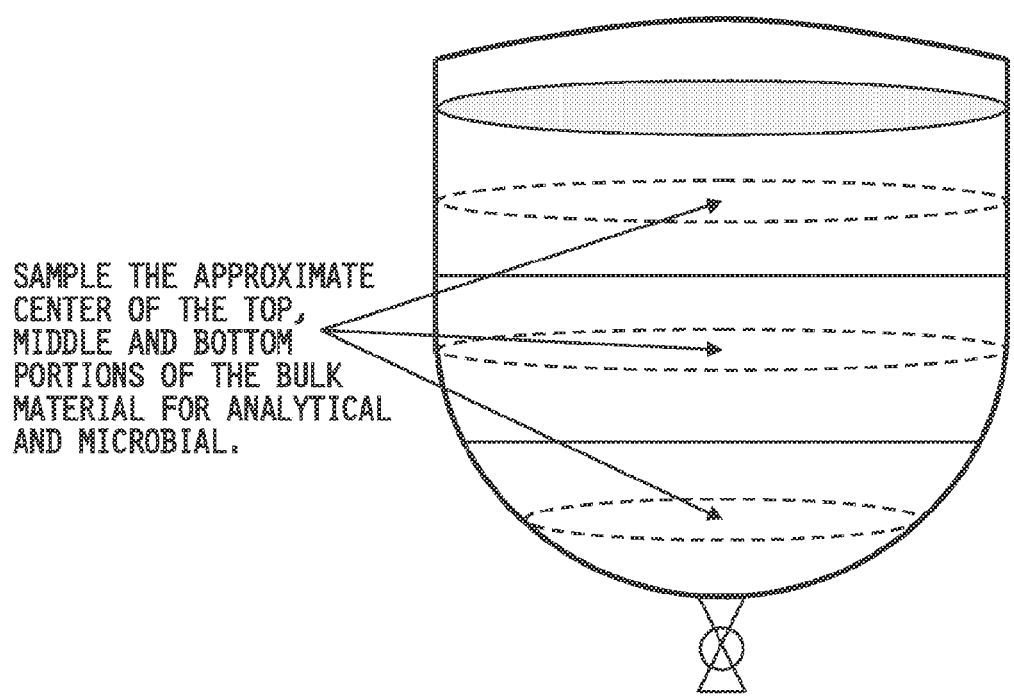
FIG. 2. Alternative Example Sampling Locations in a holding vessel.

Bulk Hold Reports for Development Batches of Placebo (no active) and Active at 500 kg scale and Process Validation Studies at 500 kg scale according to the above protocol met the product specifications, without lack of stability or uniformity, as demonstrated in the tables below, which show results following a hold at ambient temperature for portions transferred to smaller stainless steel vessels from the final holding kettle (following the at least 24 hour hold in the cold room) and sampled as indicated in FIG. 2:

| | Triptorelin Gel Placebo (Approximately 50 kg gel in a 70 L round bottom jacketed kettle) | | | | | | |
|---|---|---|---|---|---|---|---|
| | Description* | pH 5.0-6.0 | Viscosity 250-400 | Specific Gravity Report results | Triptorelin 90-110% w/w L | Sodium Methylparaben 80-120% w/w F | Sodium Propylparaben 80-120% w/w F |
| Initial | | | | | | | |
| Top 0 | Pass | 5.6 | 315 | 1.01 | Absent | 93 | 89 |
| Top 180 | | | 335 | | | 93 | 89 |
| Top Center | | | 342 | | | 93 | 89 |
| Middle 0 | Pass | 5.6 | 349 | 1.01 | Absent | 94 | 89 |
| Middle Center | | | 346 | | | 93 | 89 |
| Bottom | Pass | 5.6 | 349 | 1.01 | Absent | 93 | 89 |
| 7 Day Bulk Hold | | | | | | | |
| Top | Pass | 5.5 | 337 | 1.01 | Absent | 92 | 87 |
| Middle | Pass | 5.5 | 343 | 1.01 | Absent | 92 | 87 |
| Bottom | Pass | 5.5 | 342 | 1.01 | Absent | 92 | 87 |
| 14 Day Bulk Hold | | | | | | | |
| Top | Pass | 5.5 | 335 | 1.01 | Absent | 93 | 87 |
| Middle | Pass | 5.6 | 339 | 1.01 | Absent | 93 | 88 |
| Bottom | Pass | 5.6 | 344 | 1.01 | Absent | 93 | 88 |
| 21 Day Bulk Hold | | | | | | | |
| Top | Pass | 5.5 | 342 | 1.01 | Absent | 93 | 88 |
| Middle | Pass | 5.5 | 347 | 1.01 | Absent | 93 | 88 |
| Bottom | Pass | 5.5 | 345 | 1.01 | Absent | 93 | 88 |
| 30 Day Bulk Hold | | | | | | | |
| Top | Pass | 5.5 | 335 | 1.01 | Absent | 94 | 90 |
| Middle | Pass | 5.6 | 338 | 1.01 | Absent | 94 | 90 |
| Bottom | Pass | 5.6 | 329 | 1.01 | Absent | 93 | 90 |

*Description - Thin clear to slightly hazy gel.

Triptorelin Gel 100 μg/mL
(Approximately 20 kg gel in a 30 L round bottom jacketed kettle)

| | Description* | pH 5.0-6.0 | Viscosity 250-400 | Specific Gravity Report results | Triptorelin 90-110% w/w L | Sodium Methylparaben 80-120% w/w F | Sodium Propylparaben 80-120% w/w F |
|---|---|---|---|---|---|---|---|
| Initial | | | | | | | |
| Top 0 | Pass | 5.6 | 345 | 1.01 | 104 | 95 | 96 |
| Top 180 | | | 350 | | 106 | 95 | 97 |
| Top Center | | | 350 | | 105 | 95 | 96 |
| Middle 0 | Pass | 5.5 | 359 | 1.01 | 106 | 95 | 96 |
| Middle Center | | | 358 | | 106 | 96 | 97 |
| Bottom | Pass | 5.5 | 359 | 1.01 | 106 | 95 | 96 |
| 7 Day Bulk Hold | | | | | | | |
| Top | Pass | 5.6 | 349 | 1.01 | 105 | 94 | 96 |
| Middle | Pass | 5.6 | 356 | 1.01 | 106 | 94 | 97 |
| Bottom | Pass | 5.6 | 349 | 1.01 | 106 | 94 | 97 |
| 14 Day Bulk Hold | | | | | | | |
| Top | Pass | 5.7 | 364 | 1.01 | 106 | 94 | 96 |
| Middle | Pass | 5.6 | 372 | 1.01 | 106 | 94 | 97 |
| Bottom | Pass | 5.6 | 364 | 1.01 | 106 | 94 | 97 |
| 21 Day Bulk Hold | | | | | | | |
| Top | Pass | 5.5 | 352 | 1.01 | 105 | 93 | 94 |
| Middle | Pass | 5.5 | 354 | 1.01 | 105 | 93 | 94 |
| Bottom | Pass | 5.5 | 344 | 1.01 | 104 | 94 | 94 |

*Description - Thin clear to slightly hazy gel.

Triptorelin Gel 100 μg/mL

Approximately 60 kg Gel in a 70 L Round Stainless Steel Storage Vessel

Figure 3:
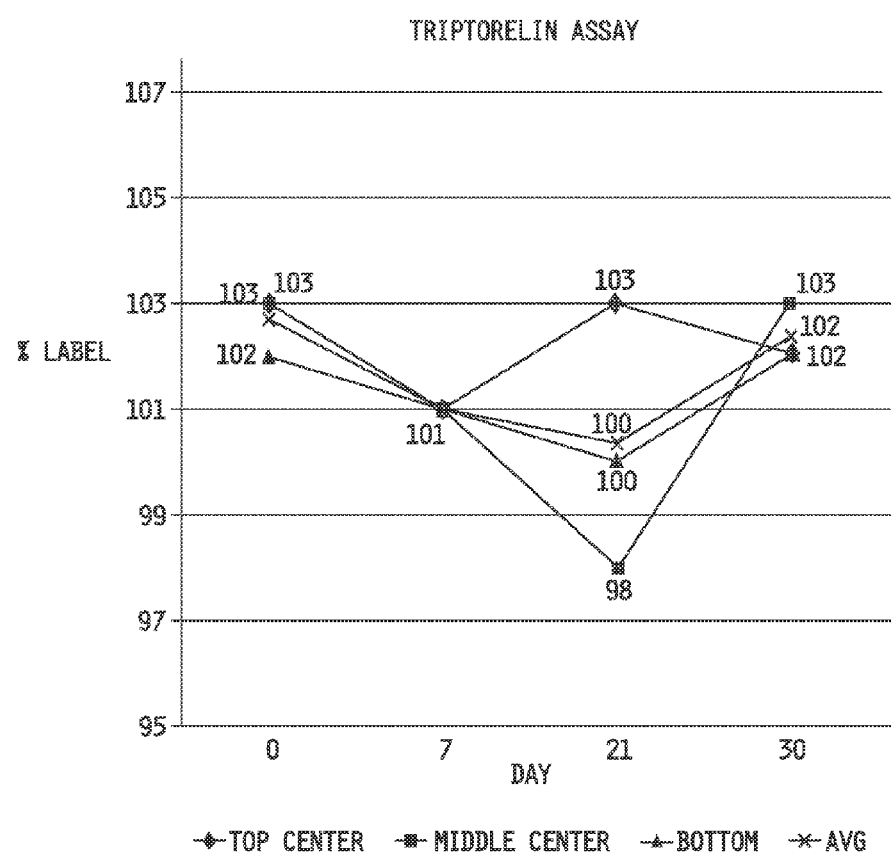
FIG. 3. Assay results for a process validation batch at days 0, 7, 21 and 30 for triptorelin.
Figure 4:
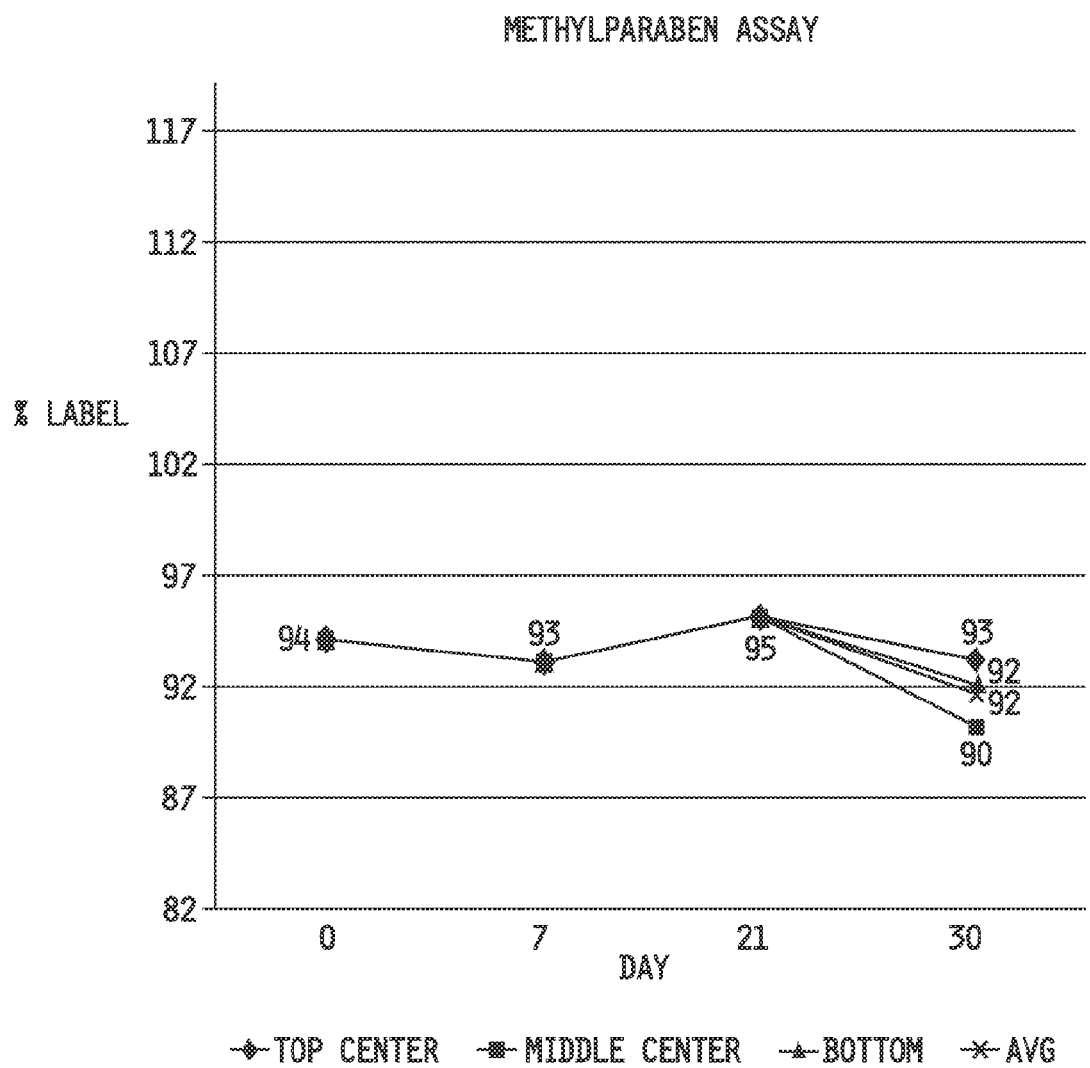
FIG. 4. Assay results for a process validation batch at days 0, 7, 21 and 30 for methyl paraben.
Figure 5:
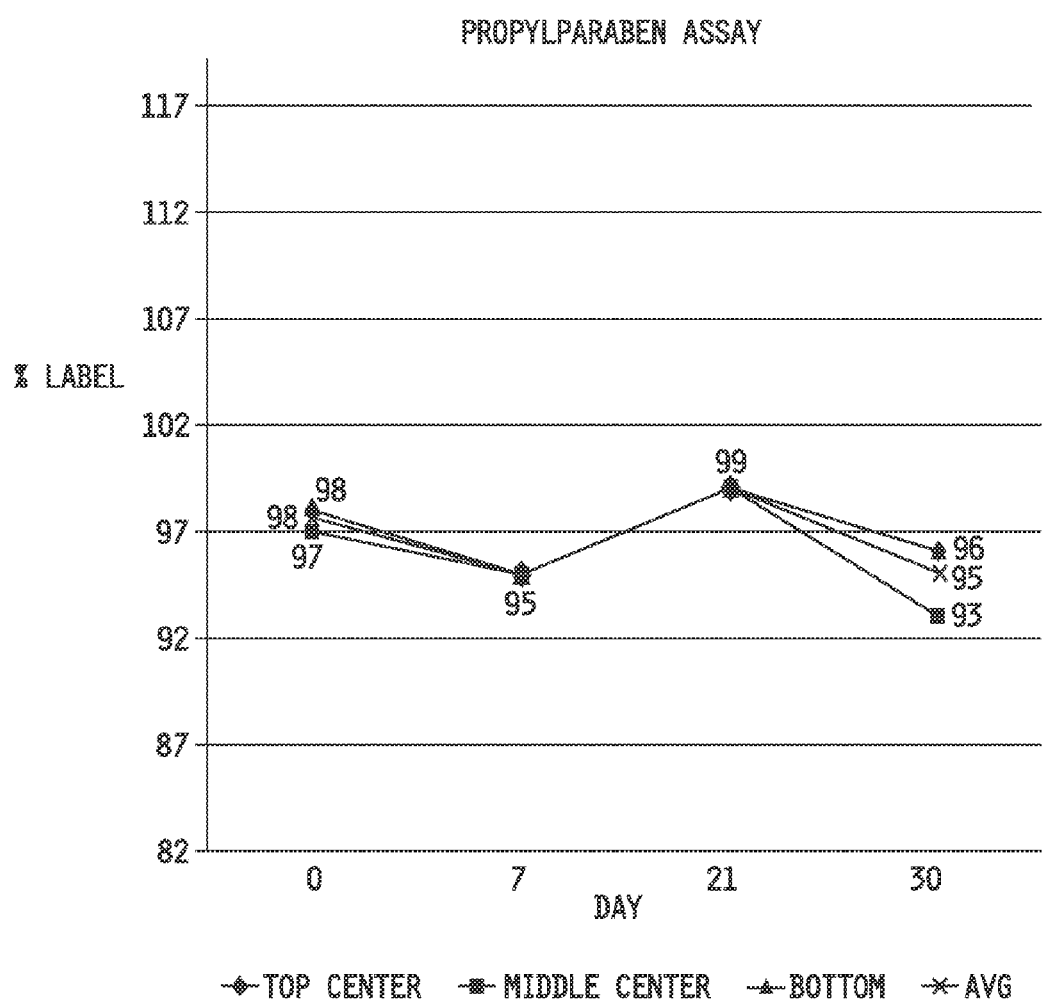
FIG. 5. Assay results for a process validation batch at days 0, 7, 21 and 30 for propyl paraben.

The assay results for batch EMCR at days 0, 7, 21 and 30 for triptorelin, methyl paraben, and propyl paraben are shown below and in FIGS. 3, 4, and 5, respectively. (Day 14 samples were not taken due to facilities work being performed in the compounding area. The area was closed and access restricted.)

Triptorelin Gel 100 μg/mL

Approximately 50 kg Gel in a 70 L Round Stainless Steel Storage Vessel

Figure 6:
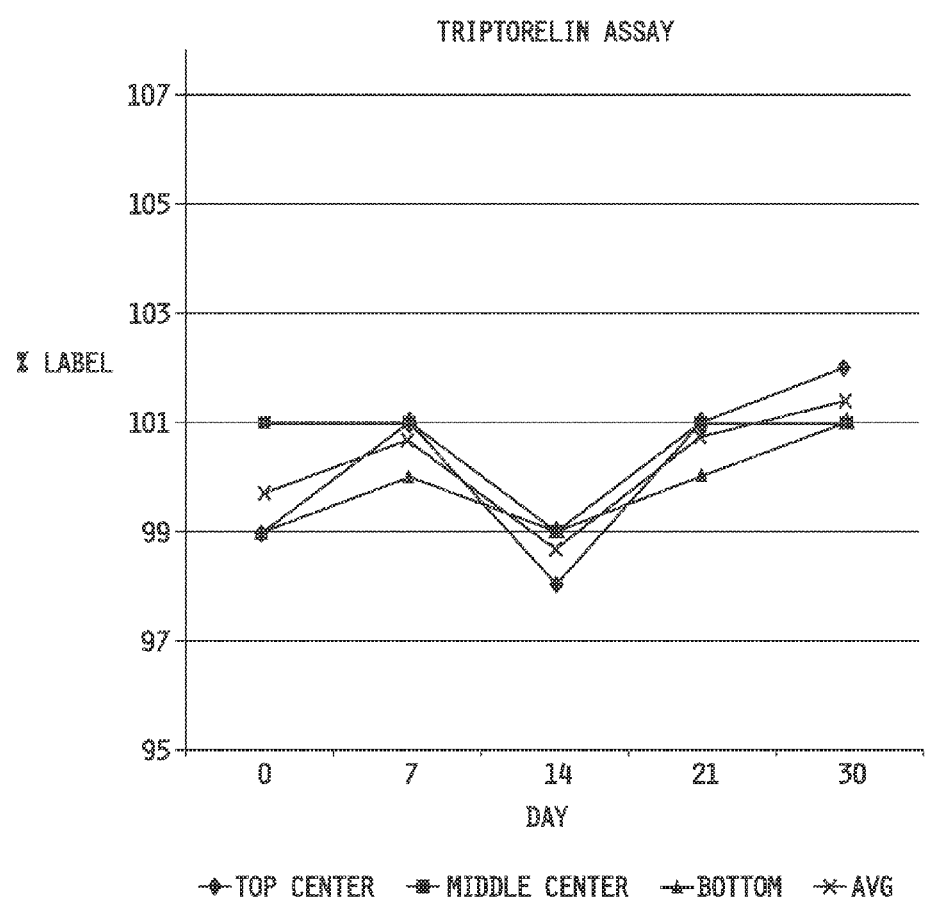
FIG. 6. Assay results for a process validation batch at days 0, 7, 14, 21 and 30 for triptorelin.
Figure 7:
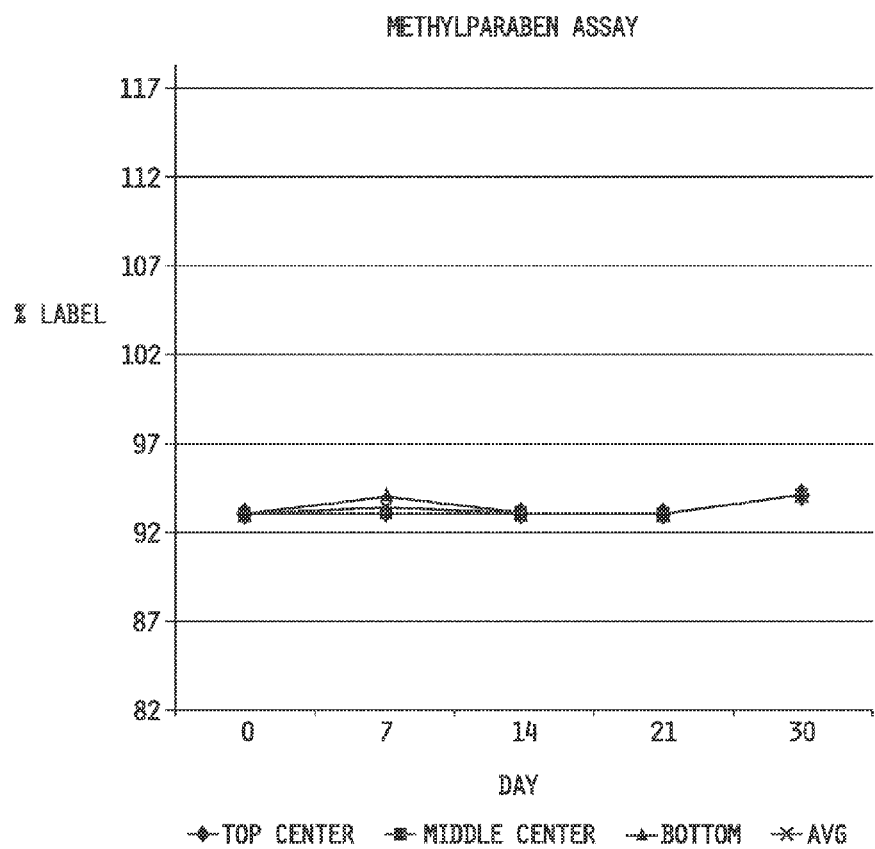
FIG. 7. Assay results for a process validation batch at days 0, 7, 14, 21 and 30 for methyl paraben.
Figure 8:
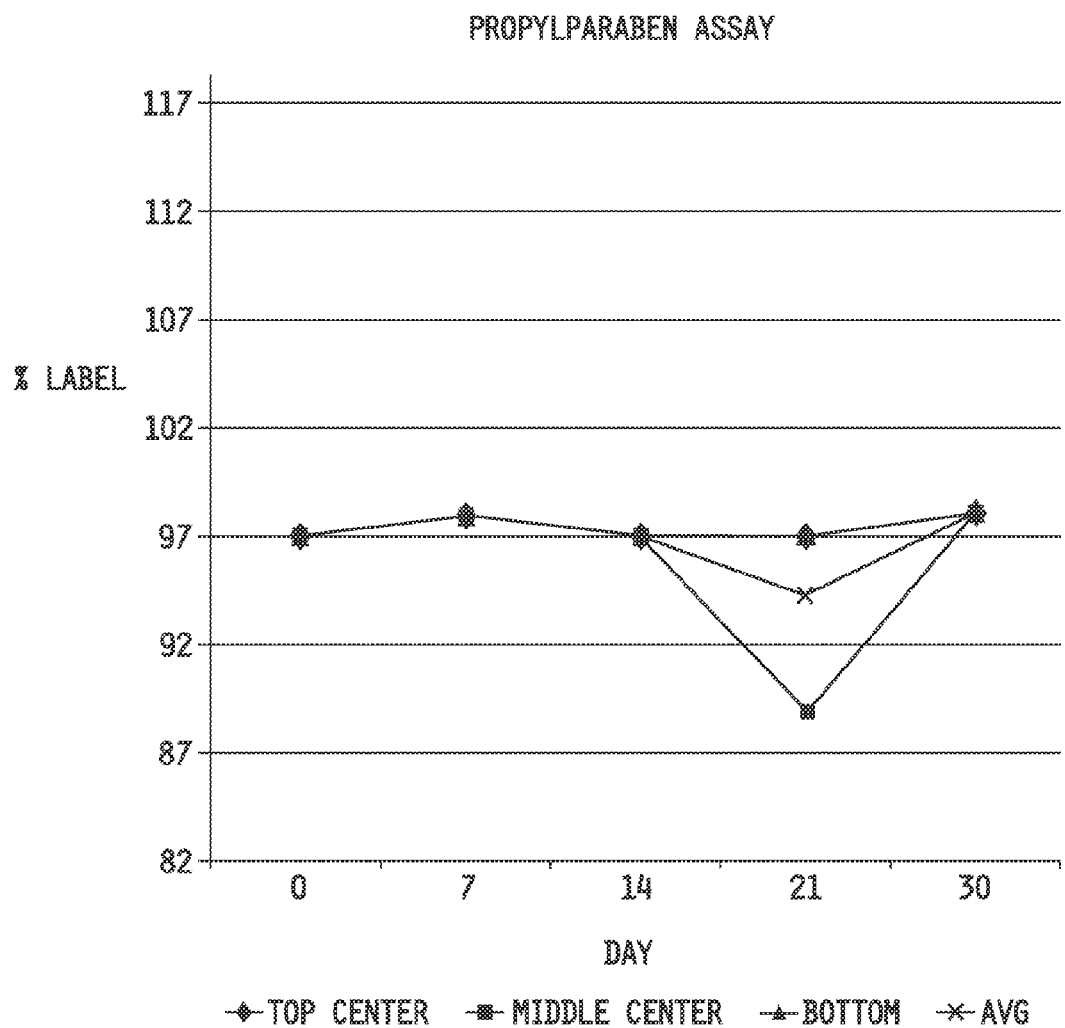
FIG. 8. Assay results for a process validation batch at days 0, 7, 14, 21 and 30 for propyl paraben.
Figure 9A:
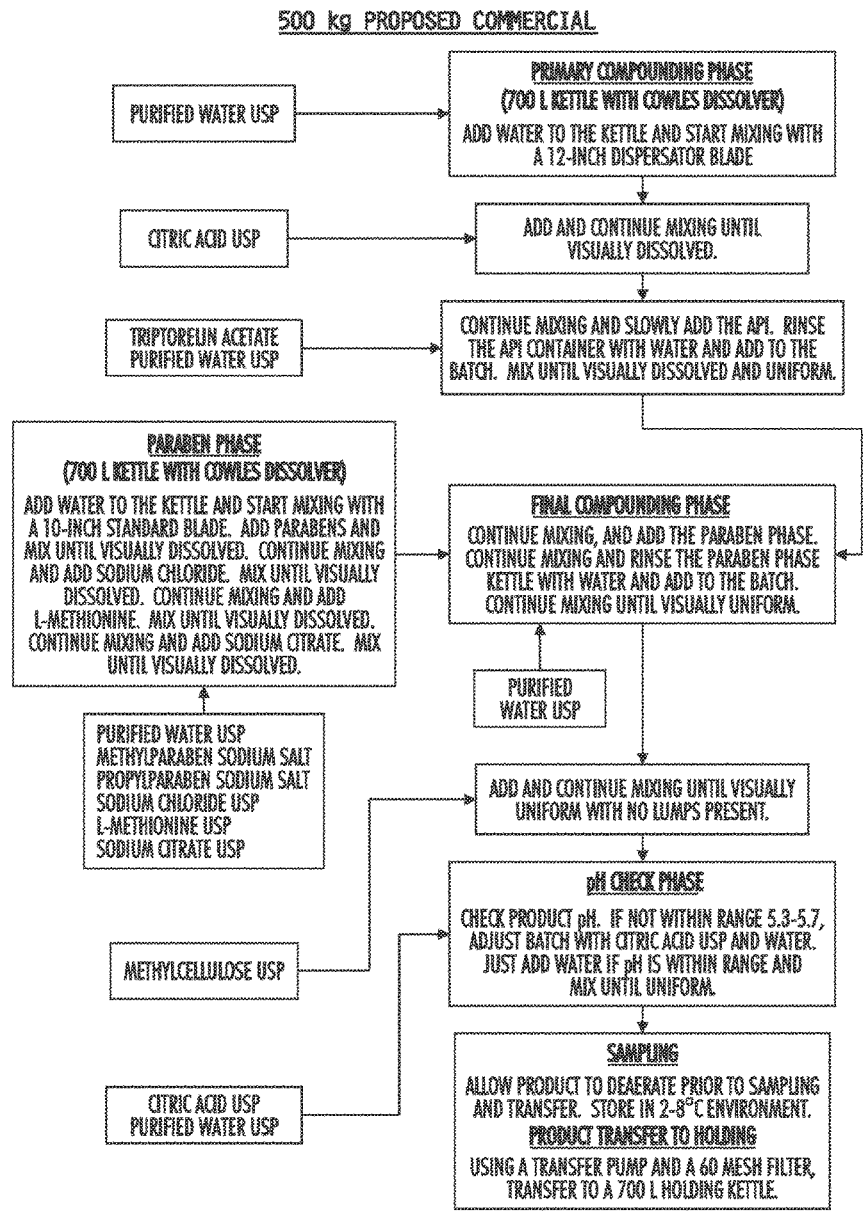
FIG. 9A.
Figure 9B:
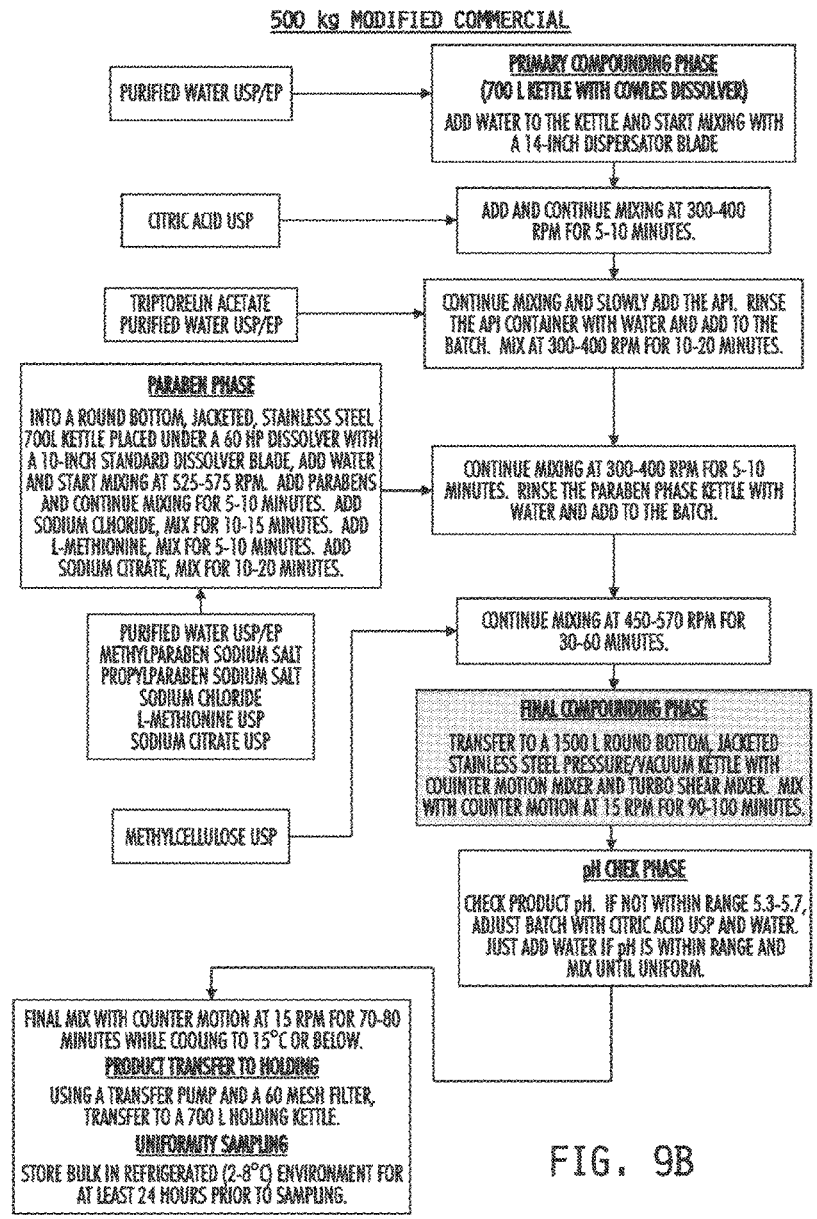
FIG. 9B. Comparison of proposed (A) and improved (modified) (B) commercial process. The manufacture is conducted in a room that blocks or does not emit UV-A, UV-B, and UV-C wavelengths.

The assay results for batch FECC at days 0, 7, 14, 21 and 30 for triptorelin, methyl paraben, and propyl paraben are shown below and in FIGS. 6, 7, and 8, respectively.

Day 0

| | | | | Results | | |
|---|---|---|---|---|---|---|
| Test | Method | Limits | Samples[7] | EMCR | FECC | Pass/Dev |
| Description[8] | 73.4009 | Pass | Top Center | Pass | Pass | Pass |
| | | | Middle Center | Pass | Pass | Pass |
| | | | Bottom | Pass | Pass | Pass |
| pH (neat) | 73.4011 | Alert Limit 5.0-5.7 | Top Center | 5.8 | 5.6 | Pass |
| | | | Middle Center | 5.6 | 5.6 | Pass |
| | | | Bottom | 5.6 | 5.5 | Pass |
| Viscosity[8] | 73.6211 | 250-400 cPs | Top Center | 371 | 348 | Pass |
| | | | Middle Center | 388 | 357 | Pass |
| | | | Bottom | 360 | 349 | Pass |
| Specific Gravity- Pycnometer | 73.0197 | Report value x.xx | Top Center | 1.01 | 1.01 | Pass |
| | | | Middle Center | 1.01 | 1.01 | Pass |
| | | | Bottom | 1.01 | 1.01 | Pass |
| Triptonelin Assay (L = 0.010% w/v) | 73.6203 | 95-108% Label RSD ≤5% | Top Center | 103 | 99 | Pass |
| | | | Middle Center | 103 | 101 | Pass |
| | | | Bottom | 102 | 99 | Pass |
| | | | % RSD | 0 | 1 | Pass |

Day 0

| Test | Method | Limits | Samples[7] | Results EMCR | Results FECC | Pass/Dev |
|---|---|---|---|---|---|---|
| Methylparaben (sodium salt) Assay (F = 0.089% w/w) | 73.6204 | 82-118% F RSD ≤5% | Top Center | 94 | 93 | Pass |
| | | | Middle Center | 94 | 93 | Pass |
| | | | Bottom | 94 | 93 | Pass |
| | | | % RSD | 0 | 0 | Pass |
| Propylparaben (sodium salt) Assay (F = 0.010% w/w) | 73.6204 | 80-120% F RSD ≤5% | Top Center | 98 | 97 | Pass |
| | | | Middle Center | 97 | 97 | Pass |
| | | | Bottom | 98 | 97 | Pass |
| | | | % RSD | 0 | 0 | Pass |

L = Label claim; F = Formula
[7]Day 0 results are Process Validation Preliminary Sampling results
[8]Thin clear to slightly hazy gel
9) Brookfield Rheometer Model DV-III, CP-40 spindle at 5 RPM @ 25° C.

Day 7

| Test | Method | Limits | Samples | Results EMCR | Results FECC | Pass/Dev. |
|---|---|---|---|---|---|---|
| Description[11] | 73.4009 | Pass | Top Center | Pass | Pass | Pass |
| | | | Middle Center | Pass | Pass | Pass |
| | | | Bottom | Pass | Pass | Pass |
| pH (neat) | 73.4011 | Alert Limit 5.0-5.7 | Top Center | 5.6 | 5.6 | Pass |
| | | | Middle Center | 5.6 | 5.6 | Pass |
| | | | Bottom | 5.6 | 5.5 | Pass |
| Viscosity[12] | 73.6211 | 250-400 cPs | Top Center | 353 | 345 | Pass |
| | | | Middle Center | 364 | 334 | Pass |
| | | | Bottom | 359 | 327 | Pass |
| Specific Gravity-Pycnometer | 73.0197 | Report value x.xx | Top Center | 1.01 | 1.01 | Pass |
| | | | Middle Center | 1.01 | 1.01 | Pass |
| | | | Bottom | 1.01 | 1.01 | Pass |
| Triptonelin Assay (L = 0.010% w/v) | 73.6203 | 90-110% Label RSD ≤5% | Top Center | 101 | 101 | Pass |
| | | | Middle Center | 101 | 101 | Pass |
| | | | Bottom | 101 | 100 | Pass |
| | | | RSD % | 0 | 0 | Pass |
| Methylparaben (sodium salt) Assay (F = 0.089% w/w) | 73.6204 | 80-120% F RSD ≤5% | Top Center | 93 | 93 | Pass |
| | | | Middle Center | 93 | 93 | Pass |
| | | | Bottom | 93 | 94 | Pass |
| | | | RSD % | 0 | 0 | Pass |
| Propylparaben (sodium salt Assay (F = 0.010% w/w) | 73.6204 | 80-120% F RSD ≤5% | Top Center | 95 | 98 | Pass |
| | | | Middle Center | 95 | 98 | Pass |
| | | | Bottom | 95 | 98 | Pass |
| | | | RSD % | 0 | 0 | Pass |

L = Label claim; F = Formula
[11]Thin clear to slightly hazy gel
[12]Brookfield Rheometer Model DV-III, CP-40 spindle at 5 RPM @ 25° C.

Day 14

| Test | Method | Limits | Samples | Results EMCR[13] | Results FECC | Pass/Dev |
|---|---|---|---|---|---|---|
| Description[14] | 73.4009 | Pass | Top Center | | Pass | Pass |
| | | | Middle Center | | Pass | Pass |
| | | | Bottom | | Pass | Pass |
| pH (neat) | 73.4011 | Alert Limit 5.0-5.7 | Top Center | | 5.6 | Pass |
| | | | Middle Center | | 5.6 | Pass |
| | | | Bottom | | 5.6 | Pass |
| Viscosity[15] | 73.6211 | 250-400 cPs | Top Center | | 330 | Pass |
| | | | Middle Center | | 327 | Pass |
| | | | Bottom | | 330 | Pass |
| Specific Gravity Pycnometer | 73.0197 | Report value x.xx | Top Center | | 1.01 | Pass |
| | | | Middle Center | | 1.01 | Pass |
| | | | Bottom | | 1.01 | Pass |

-continued

| | | Day 14 | | | |
|---|---|---|---|---|---|
| | | | | Results | |
| Test | Method | Limits | Samples | EMCR[13] FECC | Pass/Dev |
| Triptorelin Assay (L = 0.010% w/v) | 73.6203 | 95-108% Label RSD ≤5% | Top Center Middle Center Bottom % RSD | 96 99 99 0 | Pass Pass Pass Pass |
| Methylparaben (sodium salt) Assay (F = 0.089% w/w) | 73.6204 | 82-118% F RSD ≤5% | Top Center Middle Center Bottom % RSD | 93 93 93 0 | Pass Pass Pass Pass |
| Propylparaben (sodium salt) Assay (F = 0.010% w/w) | 73.6204 | 80-120% F RSD ≤5% | Top Center Middle Center Bottom % RSD | 97 97 97 0 | Pass Pass Pass Pass |

L = Label claim; F = Formula
[13]Sample not taken, see above
[14]Thin clear to slightly hazy gel
[15]Brookfield Rheometer Model DV-III, CP-40 spindle at 5 RPM @ 25° C.

| | | Day 21 | | | | |
|---|---|---|---|---|---|---|
| | | | | Results | | |
| Test | Method | Limits | Samples | EMCR | FECC | Pass/Dev. |
| Description[16] | 73.4009 | Pass | Top Center Middle Center Bottom | Pass Pass Pass | Pass Pass Pass | Pass Pass Pass |
| pH (neat) | 73.4011 | Alert Limit 5.0-5.7 | Top Center Middle Center Bottom | 5.4 5.4 5.4 | 5.6 5.6 5.6 | Pass Pass Pass |
| Viscosity[17] | 73.6211 | 250-400 cPs | Top Center Middle Center Bottom | 358 363 358 | 325 328 328 | Pass Pass Pass |
| Specific Gravity-Pycnometer | 73.0197 | Report value x.xx | Top Center Middle Center Bottom | 1.01 1.01 1.01 | 1.01 1.01 1.01 | Pass Pass Pass |
| Triptonelin Assay (L = 0.010% w/v) | 73.6203 | 90-110% Label RSD ≤5% | Top Center Middle Center Bottom RSD % | 103 98 100 2 | 101 101 100 1 | Pass Pass Pass Pass |
| Methylparaben (sodium salt) Assay (F = 0.069% w/w) | 73.6204 | 80-120% F RSD ≤5% | Top Center Middle Center Bottom RSD % | 95 95 95 0 | 93 93 93 0 | Pass Pass Pass Pass |
| Propylparaben (sodium salt) Assay (F = 0.010% w/w) | 73.6204 | 60-120% F RSD ≤5% | Top Center Middle Center Bottom RSD % | 99 99 99 0 | 97 89 97 5 | Pass Pass Pass Pass |

L = Label claim; F = Formula
[16]Thin clear to slightly hazy gel
[17]Brookfield Rheometer Model DV-III, CP-40 spindle at 5 RPM @ 25° C.

| | | Day 30 | | | | |
|---|---|---|---|---|---|---|
| | | | | Results | | |
| Test | Method | Limits | Samples | EMCR | FECC | Pass/Dev. |
| Description[18] | 73.4009 | Pass | Top Center Middle Center Bottom | Pass Pass Pass | Pass Pass Pass | Pass Pass Pass |
| pH (neat) | 73.4011 | Alert Limit 5.0-5.7 | Top Center Middle Center Bottom | 5.5 5.5 5.5 | 5.6 5.6 5.6 | Pass Pass Pass |

-continued

Day 30

| Test | Method | Limits | Samples | Results EMCR | Results FECC | Pass/Dev. |
|---|---|---|---|---|---|---|
| Viscosity[19] | 73.6211 | 250-400 cPa | Top Center | 340 | 336 | Pass |
| | | | Middle Center | 346 | 355 | Pass |
| | | | Bottom | 351 | 357 | Pass |
| Specific Gravity-Pycnometer | 73.0197 | Report value x.xx | Top Center | 1.01 | 1.01 | Pass |
| | | | Middle Center | 1.01 | 1.01 | Pass |
| | | | Bottom | 1.01 | 1.01 | Pass |
| Triptonelin Assay (L = 0.010% w/v) | 73.6203 | 90-110% Label RSD ≤5% | Top Center | 102 | 102 | Pass |
| | | | Middle Center | 103 | 101 | Pass |
| | | | Bottom | 102 | 101 | Pass |
| | | | RSD % | 1 | 1 | Pass |
| Methylparaben (sodium salt) Assay (F = 0.089% w/w) | 73.6204 | 80-120% F RSD ≤5% | Top Center | 93 | 94 | Pass |
| | | | Middle Center | 90 | 94 | Pass |
| | | | Bottom | 92 | 94 | Pass |
| | | | RSD % | 2 | 0 | Pass |
| Propylparaben (sodium salt) Assay (F = 0.010% w/w | 3.6204 | 80-120% F RSD ≤5% | Top Center | 96 | 98 | Pass |
| | | | Middle Center | 93 | 98 | Pass |
| | | | Bottom | 96 | 98 | Pass |
| | | | RSD % | 2 | 0 | Pass |

L = Label claim; F = Formula
[18]Thin clear to slightly hazy gel
[19]Brookfield Rheometer Model DV-III, CP-40 spindle at 5 RPM @ 25° C.

EXAMPLE

Description of Manufacturing Process and Process Controls for 500-Kg Commercial Batch Size (Ovugel™, Triptorelin Gel 100 μG/ml)

The manufacturing process for the 500-kg commercial batch size for Triptorelin Gel was modified as described in Example 2, above. The modifications allow for preparation of a larger batch size with the need for additional mixing and cooling. There were no changes to the formulation, specifications, methods, raw materials, or manufacturing site. The preliminary (bulk), release and stability data for batches indicated that there was no adverse effect on the identity, strength, quality, purity, or potency of the drug product by the modified manufacturing process.

The modifications to the process include an additional mixing step as the final compounding process step with a counter motion mixer and cooling of the batch. After all chemical components were added and mixed in the primary compounding phase, the batch was transferred to the vessel with counter motion mixing capability, mixed under passive vacuum, and then cooled with chilled water to 15° C. or below. The batch was then transferred to a 700 L vessel. The batch was stored in cold storage (2° C. to 8° C.) for at least 24 hours until ready for packaging. In addition, the size of the dispersator blade for the primary compounding phase was increased to 14-inch dispersator blade to more adequately mix the larger volume of product, and the paraben phase was transferred to the final compounding phase using a pump due to the larger volume of product. The additional mixing and cooling provided adequate mixing and sufficient time to cool the batch and hydrate the methylcellulose due to the larger batch size. The passive vacuum assisted in deaerating the product.

The additional mixing and cooling steps have been shown to have no adverse effect on the identity, strength, quality, purity, or potency of the drug product as evidenced by the stability data for the two 500-kg batches manufactured with the revised process.

A process and equipment comparison of the proposed 500-kg drug product manufacturing process and the modified 500-kg commercial process is provided in Tables 1-4.

TABLE 1

Process and Equipment Comparison: Paraben Phase
Table 3.2.P.3.3.1-1: Process and Equipment Comparison

| Process Step Paraben Phase | Proposed 500-kg process | Modified 500-kg process | Change |
|---|---|---|---|
| Into the Paraben Phase Kettle add Purified Water USP/EP. Place under dissolver, begin mixing and add Methylparaben Sodium Salt and Propylparaben Sodium Salt. Mix until salts are dissolved. | | | Defined parameters |
| Kettle | 700 L round bottom, jacketed kettle | 700 L round bottom, jacketed kettle | |
| Mix speed | Not defined (20-60 HP Cowles Dissolver w/10-15 inch standard blade) | 525-575 RPM (60 HP Cowles Dissolver w/10-inch standard blade) | |
| Time | Not defined | 5-10 minutes | |
| Mix and add Sodium Chloride USP. | | | Defined parameters |
| Mix speed | Not defined | 525-575 RPM | |
| Time | Not defined | 10-15 minutes | |
| Mix and add L-Methionine USP. | | | Defined parameters |
| Mix speed | Not defined | 525-575 RPM | |
| Time | Not defined | 5-10 minutes | |
| Mix and add Sodium Citrate USP. | | | Defined parameters |
| Mix speed | Not defined | 525-575 RPM | |
| Time | Not defined | 10-20 minutes | |

TABLE 2

Process and Equipment Comparison: Primary Compounding Phase
Table 3.2.P.3.3.1-1: Process and Equipment Comparison

| Process Step Primary Compounding Phase | Proposed 500-kg process | Modified 500-kg process | Change |
|---|---|---|---|
| Into the Primary Compounding Phase Kettle add Purified Water USP/EP. Place under dissolver, begin mixing and add Citric Acid USP. Mix until dissolved. | | | Changed from a 12-inch dispersator blade to a 14-inch dispersator blade and defined parameters due to size of batch |
| Kettle | 700 L round bottom, jacketed kettle | 700 L round bottom, jacketed kettle | |
| Mix speed | Not defined (25-60 HP Cowles Dissolver w/12-inch dispersator blade) | 300-400 RPM (60 HP Cowles Dissolver w/14-inch dispersator blade) | |
| Time | Not defined | 5-10 minutes | |
| Mix and add Triptorelin Acetate followed with a Purified Water USP/EP rinse | | | Defined parameters |
| Mix speed | Not defined | 300-400 RPM | |
| Time | Not defined | 10-20 minutes | |
| Mix and add Paraben Phase followed with a Purified Water USP/EP rinse | | | Defined parameters. Use of transfer pump due to size of batch |
| Transfer pump | Manually transfer | Rotating lobe | |
| Mix speed | Not defined | 300-400 RPM | |
| Time | Not defined | 5-10 minutes | |
| Mix and add Methylcellulose USP | | | Defined parameters |
| Mix speed | Not defined | 300-570 RPM | |
| Mix until Methylcellulose USP is well dispersed. | | | Defined parameters |
| Mix speed | Not defined | 450-570 RPM | |
| Time | Not defined | 30-60 minutes | |

TABLE 3

Process and Equipment Comparison: Final Compounding Phase
Table 3.2.P.3.3.1-1: Process and Equipment Comparison

| Process Step Final Compounding Phase | Proposed 500-kg process | Modified 500-kg process | Change |
|---|---|---|---|
| Into the Final Compounding Phase Kettle, transfer Primary Compounding Phase followed with a Purified Water USP/EP rinse. | Not performed | | Added mixing with counter motion mixer (CMM) due to size of batch |
| Kettle | | 1500 L round bottom, jacketed, stainless steel pressure/vacuum kettle (Lee Tri-Mix) | |
| Mix speed | | 15 RPM (CMM) With 12 mm HG passive vacuum | |
| Time | | 90-100 minutes | |
| In process pH check and adjust if needed. | | | No change |
| pH range | 5.3-5.7 | 5.3-5.7 | |
| Add Purified Water USP/EP and mix while cooling to 15° C. or below. | Not performed | | Added cooling step to begin methylcellulose hydration due to size of batch |
| Mix speed | | 15 RPM (CMM) With 12 mm HG passive vacuum | |
| Time | | 70-80 minutes | |
| Temperature | | 15° C. or below | |

TABLE 4

Process and Equipment Comparison: Transfer and Holding
Table 3.2.P.3.3.1-1: Process and Equipment Comparison

| Process Step Transfer to Holding | Proposed 500-kg process | Modified 500-kg process | Change |
|---|---|---|---|
| Mix and transfer to holding. | | | Defined parameters |
| Mix speed | Not defined | 10 RPM (CMM) | |
| Transfer pump | Rotating lobe | Rotating lobe | |
| Filter | 60 mesh screen | 60 mesh screen | |
| Holding vessel | 700 L round bottom jacketed kettle | 700 L round bottom jacketed kettle | |
| Place batch into the Cold Room (2-8° C.). Store in the Cold Room for at least 24 hours prior to sampling. | | | Defined parameters |
| Time | Not defined | >24 hours | |

What is claimed is:

1. A method for the manufacture of a gonadotropin releasing hormone-containing gel composition, the method comprising the steps of:

a) providing a primary compounding mixture of a drug product comprising the gonadotropin releasing hormone in an aqueous solution, a preservative, a stabilizer, a tonicity agent, a buffering agent, and a gelling agent;

b) further mixing the mixture;

c) adjusting the pH of the mixture; and d) further mixing the mixture with cooling to about 15° C. or below for a period of at least about 70 minutes as part of a mixing step to form a more uniform mixture.

2. The method of claim 1 wherein the gonadotropin releasing hormone has the formula

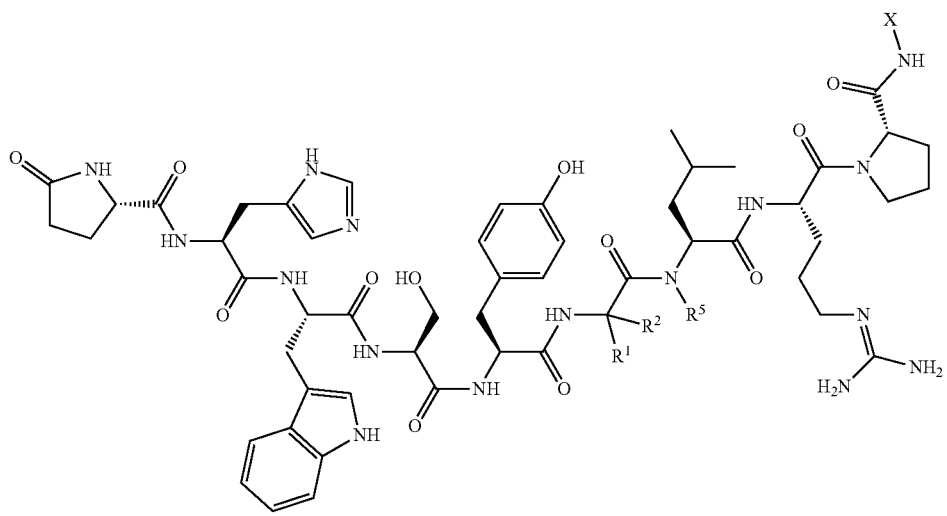

or a solvate, a hydrate, or a pharmaceutically acceptable salt thereof, wherein
- $R^1$ and $R^2$ are independently in each instance hydrogen, or are independently selected from the group consisting of alkyl, heteroalkyl, cycloalkyl, heterocycloalkyl, haloalkyl, aryl, heteroaryl, arylalkyl, and heteroarylalkyl, each of which is optionally substituted, or $R^1$ and $R^2$ and the attached carbon form a carbocycle or heterocycle;
- $R^5$ is hydrogen or alkyl; and
- X is hydrogen, or X is selected from the group consisting of alkyl, cycloalkyl, heteroalkyl, optionally substituted alkylene-carboxamide, and $HNC(O)NR^3R^4$, where $R^3$ and $R^4$ are in each instance independently selected from the group consisting of hydrogen, alkyl, heteroalkyl and haloalkyl.

3. The method of claim 1 wherein the gonadotropin-releasing hormone is selected from the group consisting of compounds of the formula of claim 2 wherein
a) $R^1$ is 1H-indol-3-yl-methyl, $R^2$ is hydrogen, X is $CH_2(CO)NH_2$; $R^5$ is hydrogen; and the configuration of the carbon to which R' is attached is R;
b) $R^1$ is hydrogen, $R^2$ is hydrogen, X is $CH_2(CO)NH_2$; and $R^5$ is hydrogen;
c) $R^1$ is 1H-1-benzyl-imidazol-4-yl-methyl, $R^2$ is hydrogen, X is ethyl; and $R^5$ is hydrogen;
d) $R^1$ is 2-methylpropyl, $R^2$ is hydrogen, X is ethyl; and $R^5$ is hydrogen;
e) $R^1$ is 2-naphthylmethyl, $R^2$ is hydrogen, X is $CH_2(CO)NH_2$; and $R^5$ is hydrogen;
f) $R^1$ is t-butoxymethyl, $R^2$ is hydrogen, X is ethyl; $R^5$ is hydrogen; and the configuration of the carbon to which R' is attached is R;
g) $R^1$ is benzyl, $R^2$ is hydrogen, X is $CH_2(CO)NH_2$; $R^5$ is hydrogen; and the configuration of the carbon to which R' is attached is R;
h) $R^1$ is t-butoxymethyl, $R^2$ is hydrogen, X is $HN(CO)NH_2$; and $R^5$ is hydrogen;
i) $R^1$ is 1H-indol-3-yl-methyl, $R^2$ is hydrogen, X is ethyl; and $R^5$ is hydrogen;
j) $R^1$ is methyl, $R^2$ is hydrogen, X is hydrogen; $R^5$ is hydrogen; and the configuration of the carbon to which $R^1$ is attached is R;
k) $R^1$ is 1H-indol-3-yl-methyl, $R^2$ is hydrogen, X is ethyl; $R^5$ is methyl; and the configuration of the carbon to which $R^1$ is attached is R;
l) $R^1$ is methyl, $R^2$ is hydrogen, X is $CH_2(CO)NH_2$; $R^5$ is hydrogen; and the configuration of the carbon to which $R^1$ is attached is R;
m) $R^1$ is 4-aminobutyl, $R^2$ is hydrogen, X is $HN(CO)NH_2$; $R^5$ is hydrogen; and the configuration of the carbon to which $R^1$ is attached is R;
n) $R^1$ is methyl, $R^2$ is methyl, X is $HN(CO)NH_2$; and $R^5$ is hydrogen; and
o) $R^1$ is ethyl, $R^2$ is hydrogen, X is hydrogen; $R^5$ is hydrogen; and the configuration of the carbon to which $R^1$ is attached is R.

4. The method of claim 1 wherein the gonadotropin-releasing hormone is triptorelin.

5. The method of claim 1 wherein the gonadotropin-releasing hormone is in acetate form.

6. The method of claim 1 wherein the preservative is selected from the group consisting of methylparaben and propylparaben.

7. The method of claim 1 wherein the stabilizer is L-methionine.

8. The method of claim 1 wherein the tonicity agent is sodium chloride.

9. The method of claim 1 wherein the buffering agent is sodium citrate-citric acid.

10. The method of claim 1 wherein the gelling agent is a polysaccharide selected from the group consisting of celluloses, dextrans, and alginates.

11. The method of claim 10 wherein the gelling agent is a cellulose and the cellulose is methylcellulose.

12. The method of claim 11 wherein the mixture comprises about 0.5 weight % to about 4.0 weight % of methylcellulose.

13. The method of claim 11 wherein the mixture comprises about 1.2 weight % of methylcellulose.

14. The method of claim 1 wherein the mixture has a pH of about 5 to about 6.

15. The method of claim 1 wherein the gonadotropin-releasing hormone is at a concentration of about 0.1% to about 5% weight/weight of the gonadotropin releasing hormone-containing gel composition.

16. The method of claim 1 wherein the gelling agent is methylcellulose and the methylcellulose is present in an amount that provides a viscosity of about 250 cP to about 400 cP.

17. The method of claim 1 comprising mixing the mixture using counter motion mixing.

* * * * *